(12) United States Patent
Elshourbagy et al.

(10) Patent No.: US 10,259,804 B2
(45) Date of Patent: Apr. 16, 2019

(54) ANTI-ENDOTHELIAL LIPASE COMPOUNDS AND METHODS OF USING THE SAME IN THE TREATMENT AND/OR PREVENTION OF CARDIOVASCULAR DISEASES

(71) Applicant: Shifa Biomedical Corporation, Malvern, PA (US)

(72) Inventors: Nabil Elshourbagy, West Chester, PA (US); Shaker Mousa, Wynantskill, NY (US); Harold Meyers, Weston, MA (US)

(73) Assignee: SHIFA BIOMEDICAL CORPORATION, Malvern, PA (US)

( * ) Notice: Subject to any disclaimer, the term of this patent is extended or adjusted under 35 U.S.C. 154(b) by 0 days.

(21) Appl. No.: 15/514,157

(22) PCT Filed: Sep. 23, 2015

(86) PCT No.: PCT/US2015/051630
§ 371 (c)(1),
(2) Date: Mar. 24, 2017

(87) PCT Pub. No.: WO2016/049128
PCT Pub. Date: Mar. 31, 2016

(65) Prior Publication Data
US 2017/0305887 A1    Oct. 26, 2017

Related U.S. Application Data

(60) Provisional application No. 62/055,817, filed on Sep. 26, 2014.

(51) Int. Cl.
*C07D 405/12* (2006.01)
*C07D 405/14* (2006.01)
*C07D 307/66* (2006.01)

(52) U.S. Cl.
CPC ......... *C07D 405/12* (2013.01); *C07D 307/66* (2013.01); *C07D 405/14* (2013.01)

(58) Field of Classification Search
CPC .................................................. C07D 405/12
See application file for complete search history.

(56) References Cited

U.S. PATENT DOCUMENTS

| | | |
|---|---|---|
| 2006/0014794 A1 | 1/2006 | Chao et al. |
| 2007/0248594 A1 | 10/2007 | Chao et al. |
| 2009/0111794 A1 | 4/2009 | Bacani et al. |

FOREIGN PATENT DOCUMENTS

| | | |
|---|---|---|
| WO | 2007/010546 A1 | 1/2007 |
| WO | 2015/054117 A1 | 4/2015 |

OTHER PUBLICATIONS

Goodman, Bioorganic & Medicinal Chemistry Letters 19 (2009) 27-30.*
Kovacic. Circulation, 125, 1795-1808. (Year: 2012).*
Jantzen. Modern Pharmaceutics, 596. (Year: 1996).*
Keller, P.M., et al., "A High-Throughput Screen for Endothelial Lipase Using HDL as Substrate" J. Biomolecular Screening (2008) 13(6):468-475.
Choi, S.Y., et al., "Endothelial lipase: a new lipase on the block" J. Lipid Research (2002) 43:1763-1769.
Cox, L.A, et al., "Identification of Promoter Variants in Baboon Endothelial Lipase That Regulate High-Density Lipoprotein Cholesterol Levels" Circulation (2007) 116:1185-1195.
Badellino, K.O., et al., "Endothelial Lipase Concentrations Are Increased in Metabolic Syndrome and Associated with Coronary Atherosclerosis" PLoS Med. (2006) 3(2):e22.
Jin, W., et al., "Inhibition of endothelial lipase causes increased HDL cholesterol levels in vivo" J. Clin. Invest. (2003) 111(3):357-62.
Otera, H., et al., "Targeted inactivation of endothelial lipase attenuates lung allergic inflammation through raising plasma HDL level and inhibiting eosinophil infiltration" Am. J. Physiol. Lung Cell Mol. Physiol. (2009) 296(4):L594-602.
Ishida, T., et al., "Endothelial lipase modulates susceptibility to atherosclerosis in apolipoprotein-E-deficient mice" J. Biol. Chem. (2004) 279(43):45085-92.
Hara, T., et al., "Targeted deletion of endothelial lipase increases HDL particles with anti-inflammatory properties both in vitro and in vivo" J. Lipid Res. (2011) 52(1):57-67.
Yasuda, T., et al., "Update on the role of endothelial lipase in high-density lipoprotein metabolism, reverse cholesterol transport, and atherosclerosis" Circ. J. (2010) 74(11):2263-70.
Ma, K., et al., "Endothelial lipase is a major genetic determinant for high-density lipoprotein concentration, structure, and metabolism" Proc. Natl. Acad. Sci., (2003) 100(5)2748-53.

* cited by examiner

*Primary Examiner* — Noble E Jarrell
(74) *Attorney, Agent, or Firm* — Robert C. Netter, Jr.; Dann, Dorfman, Herrell & Skillman

(57) ABSTRACT

Endothelial Lipase (EL) inhibitors and methods of using such inhibitors for treating conditions implicating EL are provided herein. The present invention meets the needs in the field by providing small molecule inhibitors of EL function that can be used therapeutically to raise HDL cholesterol levels in blood, and can be used in the prevention and/or treatment of cholesterol and lipoprotein metabolism disorders, including, but not limited to, familial hypercholesterolemia, atherogenic dyslipidemia, atherosclerosis, and, more generally, cardiovascular disease (CVD).

5 Claims, 27 Drawing Sheets

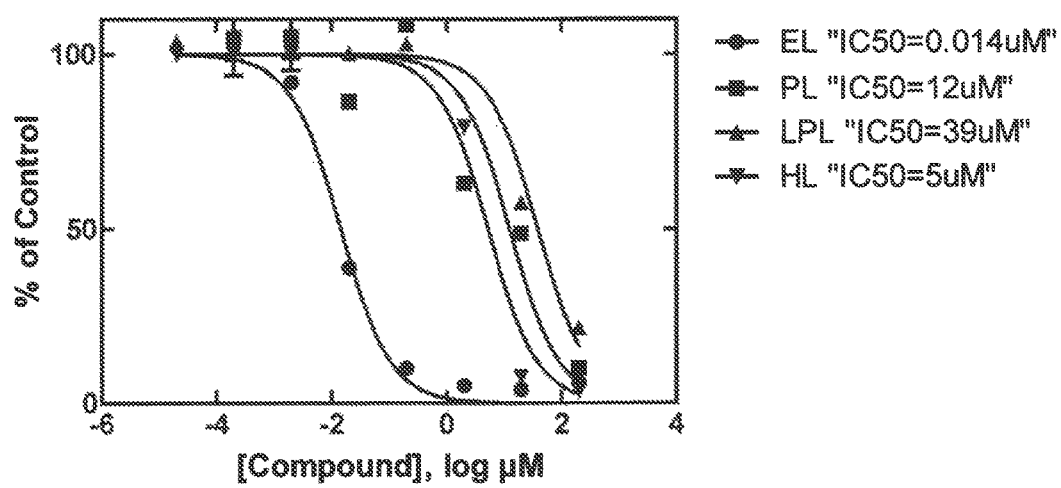
Figure 3A (SBC-140,239)

Figure 3B (SBC-140,241)
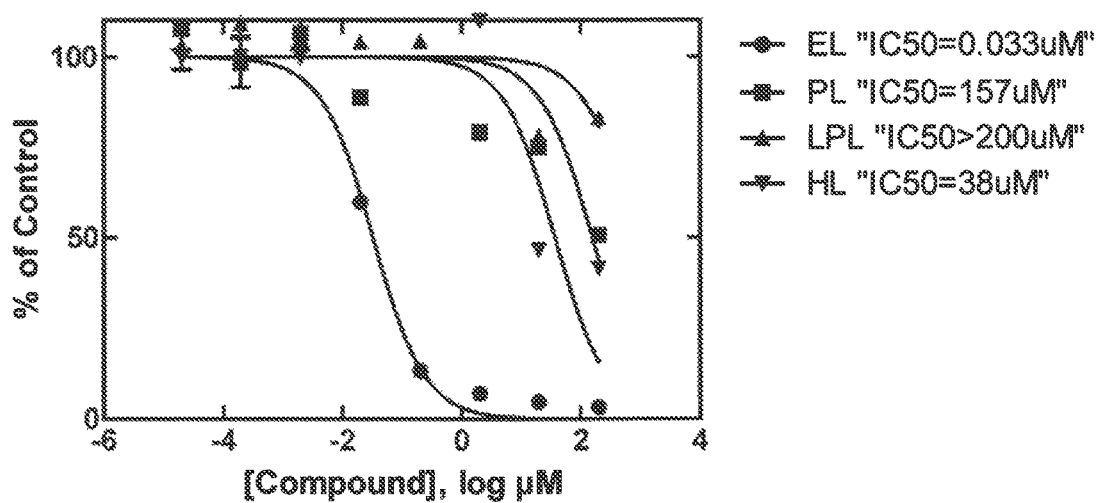

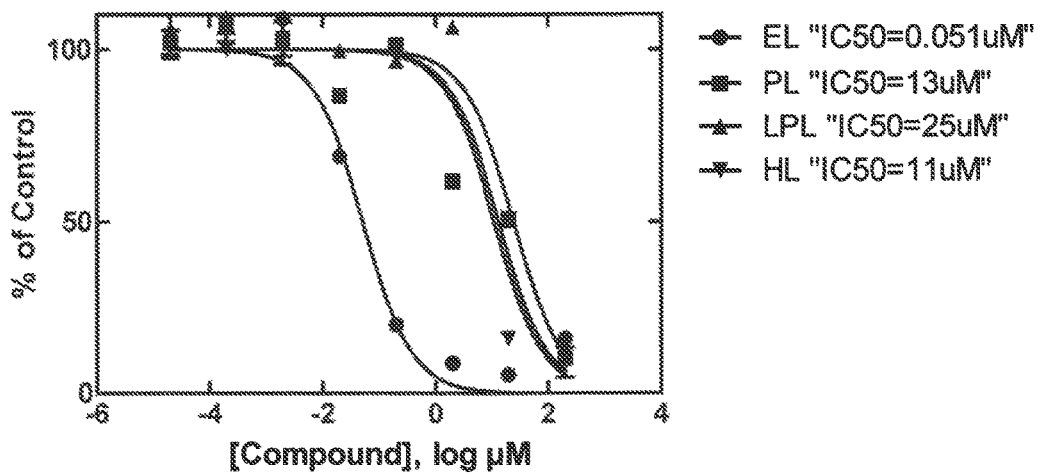
Figure 3C (SBC-140,244)

Figure 4

| SBC Code | EL_IC50 (uM) | PL_IC50 (uM) | LPL_IC50 (uM) | HL_IC50 (uM) |
|---|---|---|---|---|
| SBC-140,239 | 0.014 | 12 | 39 | 5 |
| SBC-140,241 | 0.033 | >100 | >200 | 38 |
| SBC-140,244 | 0.051 | 13 | 25 | 11 |
| SBC-140,209 | 0.06 | >100 | >100 | Not tested |
| SBC-140,210 | 0.1 | >100 | >100 | Not tested |
| SBC-140,242 | 0.1 | Not tested | Not tested | Not tested |
| SBC-140,002 | 0.11 | 130 | 855 | Not tested |
| SBC-140,204 | 0.15 | >100 | >100 | Not tested |
| SBC-140,212 | 0.17 | >100 | >100 | Not tested |
| SBC-140,240 | 0.18 | Not tested | Not tested | Not tested |
| SBC-140,205 | 0.21 | >100 | >100 | Not tested |
| SBC-140,250 | 0.21 | Not tested | Not tested | Not tested |
| SBC-140,245 | 0.22 | Not tested | Not tested | Not tested |
| SBC-140,248 | 0.25 | Not tested | Not tested | Not tested |
| SBC-140,246 | 0.34 | Not tested | Not tested | Not tested |
| SBC-140,208 | 0.37 | 53 | >100 | Not tested |
| SBC-140,243 | 0.38 | Not tested | Not tested | Not tested |
| SBC-140,179 | 0.4 | 4.4 | >100 | Not tested |
| SBC-140,228 | 0.76 | Not tested | Not tested | Not tested |
| SBC-140,249 | 0.77 | Not tested | Not tested | Not tested |
| SBC-140,211 | 0.87 | 29 | 67 | Not tested |
| SBC-140,175 | 1.2 | 2.8 | 12 | Not tested |
| SBC-140,180 | 2.2 | 4.9 | 4.9 | Not tested |
| SBC-140,226 | 2.5 | Not tested | Not tested | Not tested |
| SBC-140,247 | 2.7 | Not tested | Not tested | Not tested |
| SBC-140,227 | 3.4 | Not tested | Not tested | Not tested |
| SBC-140,206 | 4.2 | >100 | >100 | Not tested |
| SBC-140,460 | 0.019 | >200 | >200 | >200 |
| SBC-140,466 | 0.062 | >200 | >200 | >200 |
| SBC-140,472 | 0.072 | >200 | >200 | >200 |

Figure 6
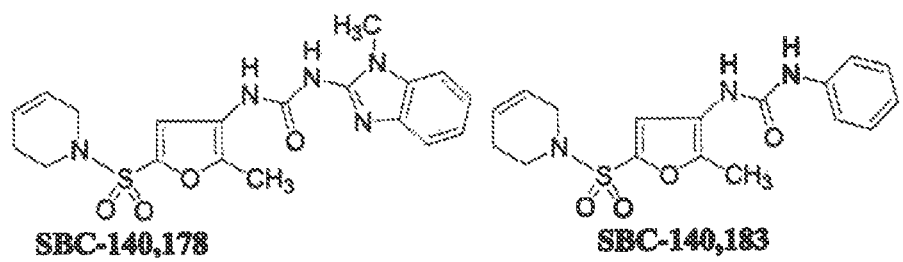
SBC-140,178        SBC-140,183
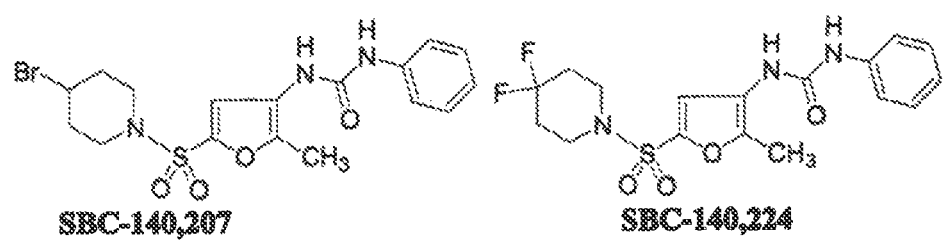
SBC-140,207        SBC-140,224
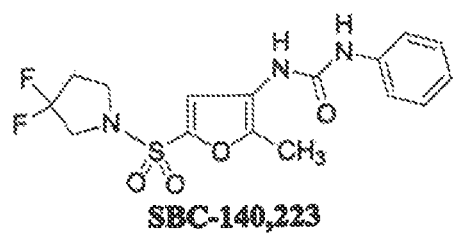
SBC-140,223

Figure 7
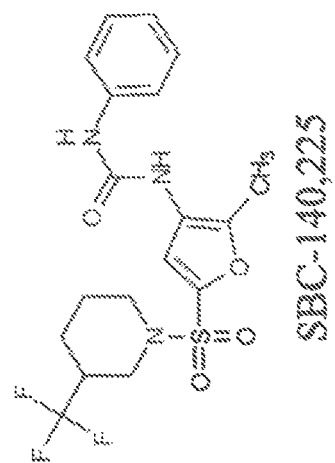
SBC-140,225
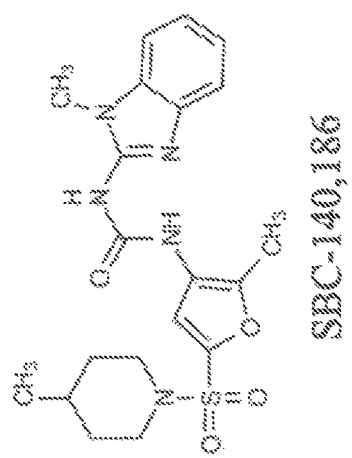
SBC-140,186
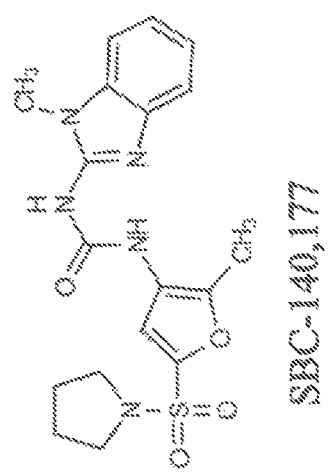
SBC-140,177

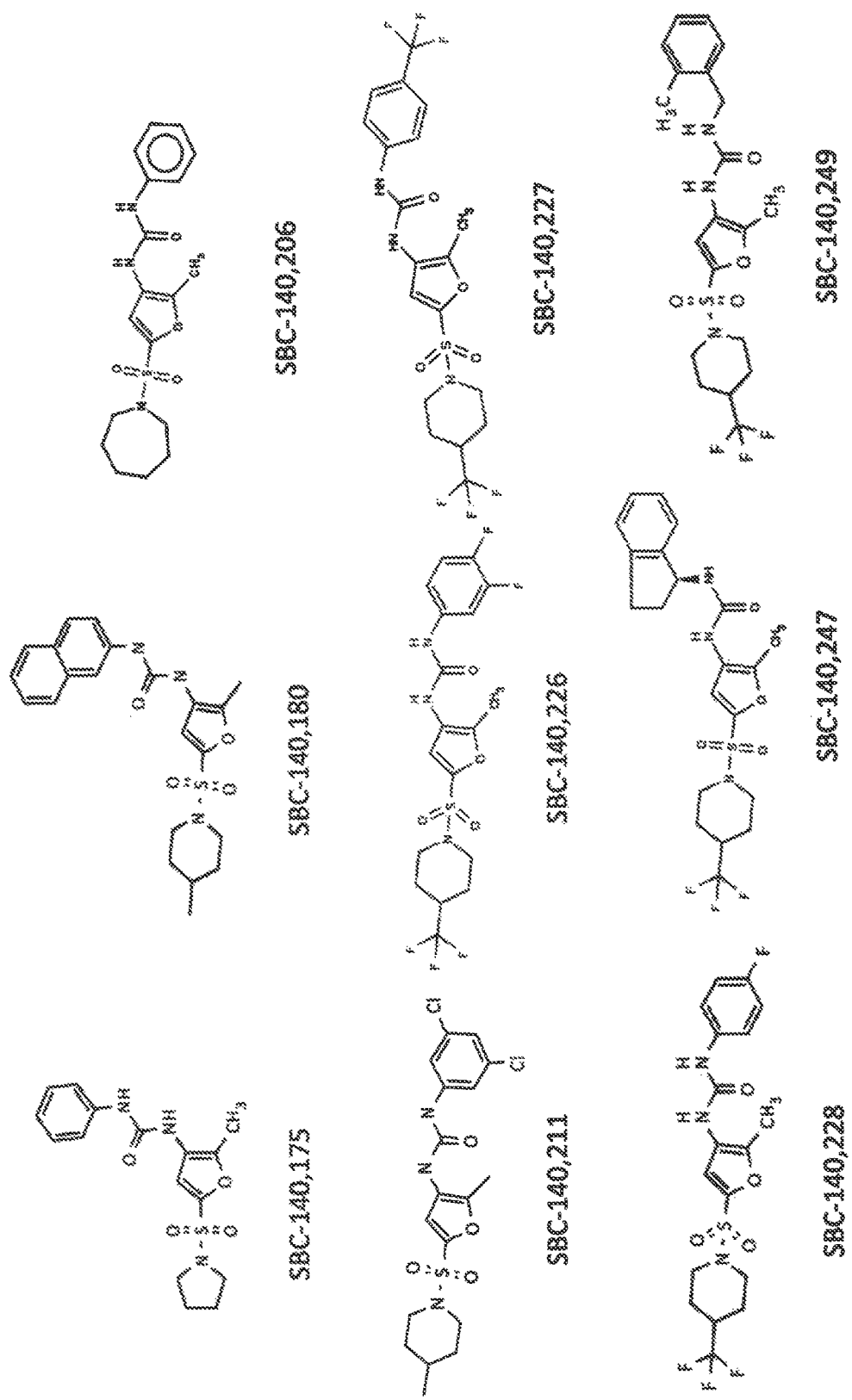

*Figure 9 (continued)*
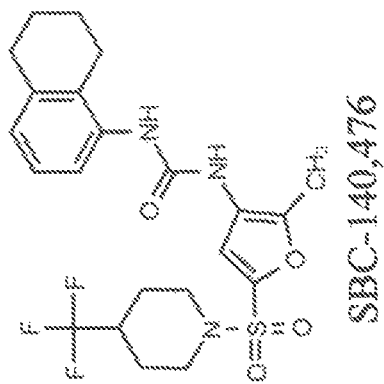
SBC-140,476
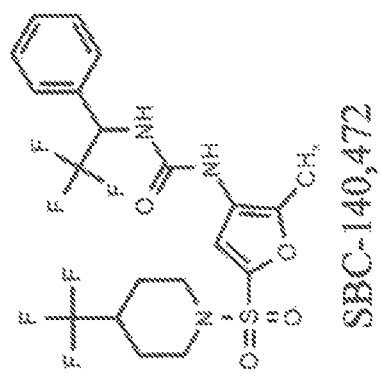
SBC-140,472
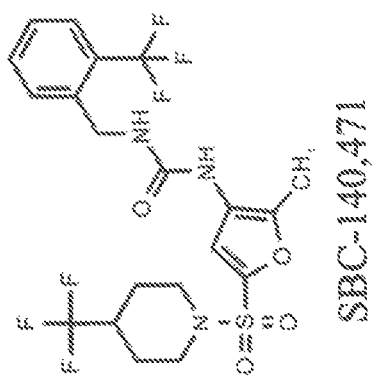
SBC-140,471

Figure 12

| Compound | EL IC50 (µM) | PL IC50 (µM) | LPL IC50 (µM) | HL IC50 (µM) |
|---|---|---|---|---|
| SBC-140,460 | 0.019 | >200 | >200 | >200 |
| SBC-140,466 | 0.062 | >200 | >200 | >200 |
| SBC-140,472 | 0.072 | >200 | >200 | >200 |

ANTI-ENDOTHELIAL LIPASE COMPOUNDS AND METHODS OF USING THE SAME IN THE TREATMENT AND/OR PREVENTION OF CARDIOVASCULAR DISEASES

CROSS-REFERENCE TO RELATED APPLICATIONS

This application is a § 371 of International Application No. PCT/US2015/051630, filed Sep. 23, 2015, which claims the benefit of U.S. Provisional Application No. 62/055,817, filed Sep. 26, 2014. The entire disclosure of each of the aforesaid applications is incorporated by reference in the present application.

GOVERNMENT LICENSE RIGHTS

The present invention was made with support from the National Heart, Lung and Blood Institute (NHLBI) under SBIR Grant No. HL097438. The U.S. Government has certain rights in this invention.

FIELD OF THE INVENTION

The present invention relates generally to compounds that inhibit the physiological action of the enzyme endothelial lipase (EL), and more particularly, but not exclusively, to compositions comprising small molecule inhibitors of EL function and methods of using these inhibitors as treatments for cardiovascular disease.

BACKGROUND OF THE INVENTION

Cardiovascular diseases are the leading cause of death in the United States. Moreover, atherosclerosis is the leading cause of cardiovascular diseases. Atherosclerosis is a disease of the arteries and is responsible for coronary heart disease associated with many deaths in industrialized countries. Atherosclerosis is an inflammatory condition resulting from multiple and cumulative risk factors, each of which contributes in varying ways to the development and severity of the condition. The risk of atherosclerosis and heart attacks is strongly correlated to blood cholesterol levels, where low-density lipoprotein (LDL) cholesterol (LDL-C) is pro-inflammatory and high-density lipoprotein (HDL) cholesterol (HDL-C) is anti-inflammatory. Several risk factors for coronary heart disease have now been identified: dyslipidemia, hypertension, diabetes, smoking, poor diet, inactivity and stress. Dyslipidemia is elevation of plasma cholesterol (hypercholesterolemia) and/or triglycerides (TGs) or a low HDL level that contributes to the development of atherosclerosis. Dyslipidemia is a metabolic disorder that is proven to contribute to cardiovascular disease. In the blood, cholesterol is transported in lipoprotein particles, where the LDL-C is considered "bad" cholesterol, while HDL-C is known as "good" cholesterol. Lipid and lipoprotein abnormalities are extremely common in the general population and are regarded as a highly modifiable risk factor for cardiovascular disease, due to the influence of cholesterol on atherosclerosis.

There is a long-felt and significant unmet need for CVD treatments with 60-70% of cardiovascular events, heart attacks and strokes occurring despite the treatment with statins (the current standard of care in atherosclerosis).

SUMMARY OF THE INVENTION

The present invention meets the needs in the field by providing small molecule inhibitors of EL function that can be used therapeutically to raise HDL-cholesterol levels in blood, and can be used in the prevention and/or treatment of cholesterol and lipoprotein metabolism disorders, including, but not limited to, familial hypercholesterolemia, atherogenic dyslipidemia, atherosclerosis, and, more generally, cardiovascular disease (CVD).

The agents or compounds (i.e., EL inhibitors) used in the practice of this invention may have the general formula (I):

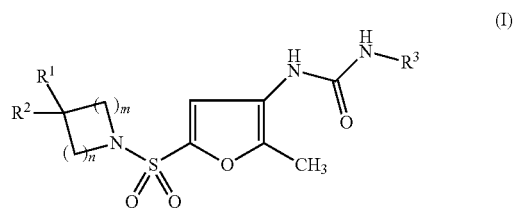

(I)

including all isomers, hydrates, solvates, pharmaceutically acceptable salts, prodrugs and complexes thereof, wherein:

$R^1$ and $R^2$ may each independently be selected from a group consisting of hydrogen, OH, $NH_2$, $NH(C_1-C_6$ alkyl), $N(C_1-C_6$ alkyl$)_2$, $NO_2$, CN, $C_1-C_3$ haloalkyl, $C_1-C_3$ haloalkoxy, SH, optionally substituted $C_1-C_6$ alkyl, optionally substituted $C_1-C_6$ alkenyl, optionally substituted $C_1-C_6$ alkynyl, optionally substituted $C_1-C_6$ alkoxy, optionally substituted $S(C_1-C_6$ alkyl), optionally substituted $C_3-C_8$ cycloalkyl, optionally substituted $C_1-C_6$ ($C_3-C_8$ cycloalkyl)alkyl, optionally substituted aryl, optionally substituted $C_1-C_6$ aralkyl, optionally substituted 3-10 membered heterocycle containing 1 to 4 heteroatoms selected from N, O and S, optionally substituted $C_1-C_6$ (heterocyclyl)alkyl, optionally substituted heteroaryl, and optionally substituted $C_1-C_6$ (heteroaryl)alkyl;

$R^3$ may be selected from a group consisting of hydrogen, optionally substituted $C_3-C_8$ cycloalkyl, optionally substituted $C_1-C_6$ ($C_3-C_8$ cycloalkyl)alkyl, optionally substituted aryl, optionally substituted $C_1-C_6$ aralkyl, optionally substituted 3-10 membered heterocycle containing 1 to 4 heteroatoms selected from N, O and S, optionally substituted $C_1-C_6$ (heterocyclyl)alkyl, optionally substituted heteroaryl, optionally substituted $C_1-C_6$ (heteroaryl)alkyl, or taken together with the atom to which they are bound to form an optionally substituted, optionally unsaturated heterocycle ring having from 3 to 7 ring atoms, and

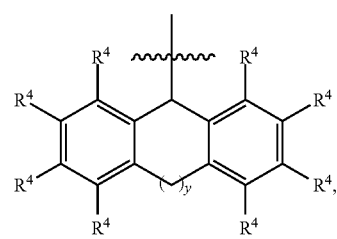

wherein $R^4$ at each occurrence may independently be selected from a group consisting of hydrogen, halogen, cyano, optionally substituted $C_1-C_6$ alkyl, optionally substituted $C_1-C_6$ alkoxy, optionally substituted $C_3-C_8$ cycloalkyl, optionally substituted aryl, optionally substituted $C_1-C_6$ aralkyl, OH, $NH_2$, $NH(C_1-C_6$ alkyl), $N(C_1-C_6$ alkyl$)_2$, $NO_2$, $C_1-C_3$ haloalkyl, $C_1-C_3$ haloalkoxy, SH, optionally substituted S($C_1$-$C_6$ alkyl), 3-10 membered heterocycle containing 1 to 4 heteroatoms selected from N, O and S, and optionally substituted heteroaryl; m=0, 1, 2, 3, or 4; n=0, 1, 2, 3, or 4; provided that m and n cannot both be zero; and y=0, 1, or 2.

In a specific embodiment of compounds having the general formula I, the present invention includes compounds wherein m+n=3-5 and $R^3$ includes at least one of an optionally substituted aryl and $C_1$-$C_6$ aralkyl.

In certain embodiments, the compounds of Formula I may include those compounds set forth in FIGS. 7, 8, and/or 9.

Additionally, in certain other embodiments, EL inhibitors of the invention may have the general formula (II):

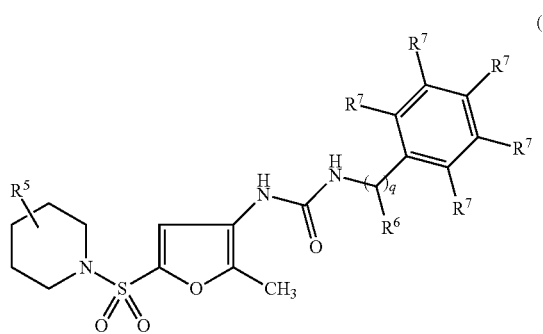

including all isomers, hydrates, solvates, pharmaceutically acceptable salts, prodrugs and complexes thereof, wherein:

$R^5$ may independently be selected from a group consisting of hydrogen, $C_1$-$C_3$ alkyl, $C_1$-$C_3$ alkoxy, and $C_1$-$C_3$ haloalkyl;

$R^6$ may independently be selected from a group consisting of hydrogen, $C_1$-$C_3$ alkyl, $C_1$-$C_3$ haloalkyl, and aryl;

$R^7$ may be selected from a group consisting of hydrogen, halogen, optionally substituted alkoxy, optionally substituted $C_1$-$C_6$ alkyl, optionally substituted $C_1$-$C_6$ alkenyl, optionally substituted $C_1$-$C_6$ alkynyl, optionally substituted $C_1$-$C_6$ alkoxyalkyl, optionally substituted $C_1$-$C_6$ aryloxyalkyl, optionally substituted $C_1$-$C_6$ alkylthioalkyl, optionally substituted $C_1$-$C_6$ arylthioalkyl, optionally substituted $C_3$-$C_8$ cycloalkyl, optionally substituted $C_1$-$C_6$ ($C_3$-$C_8$ cycloalkyl) alkyl, optionally substituted aryl, optionally substituted $C_1$-$C_6$ aralkyl, $C_1$-$C_3$ haloalkyl, $C_1$-$C_3$ haloalkoxy, optionally substituted 3-10 membered heterocycle containing 1 to 4 heteroatoms selected from N, O and S, optionally substituted $C_1$-$C_6$ (heterocyclyl)alkyl, optionally substituted heteroaryl, and optionally substituted $C_1$-$C_6$ (heteroaryl)alkyl;

$R^6$ and $R^7$ may be taken together with the atom to which they are bound to form an optionally substituted, optionally unsaturated carbocycle or heterocycle ring having from 4 to 7 ring atoms; and q=0 or 1. Moreover, at least two $R^7$ groups may be taken together to form an optionally substituted, optionally unsaturated heterocyclic ring having from 3 to 7 ring atoms.

In another aspect, the present invention sets forth a method of treating or delaying the progression of disorders alleviated by inhibiting epithelial lipase (EL) in a patient in need of said treatment, the method including administering a therapeutically effective amount of at least one compound of Formula I, and the pharmaceutically acceptable salts, isomers, hydrates, solvates, prodrugs, and complexes of said compound.

More specifically, the methods of the invention may include methods of treating or delaying disorders implicating EL, or disorders that may be ameliorated by raising HDL-cholesterol levels in blood, including, but not limited to, hypercholesterolemia, atherosclerosis, low HDL cholesterol, dyslipidemia, cardiovascular disease (CVD), coronary heart disease, and combinations thereof. The methods of the invention may also include methods of treating, delaying, and/or preventing cholesterol and lipoprotein metabolism disorders.

In another embodiment, the methods of the invention may include administering a therapeutically effective amount of at least one compound of Formula I, wherein m+n=3-5 and/or $R^3$ may include an optionally substituted aryl or optionally substituted $C_1$-$C_6$ aralkyl.

In a further embodiment, the method of the invention may include administering a therapeutically effective amount of at least one compound of Formula II, and the pharmaceutically acceptable salts, isomers, hydrates, solvates, prodrugs, and complexes of said compound.

Additionally, the methods of the invention may include administering a therapeutically effective amount of at least one compound described in FIGS. 6 to 9. In certain preferred embodiments, the methods of the invention may include administering a therapeutically effective amount of at least one compound described in FIG. 9.

BRIEF DESCRIPTION OF THE DRAWINGS

The foregoing summary and the following detailed description of the exemplary embodiments of the present invention may be further understood when read in conjunction with the appended figures, in which:

FIGS. 3A to 3C graphically illustrate the effect of various concentrations of SBC-140,239 (FIG. 3A), SBC-140,241 (FIG. 3B) and SBC-140,244 (FIG. 3C) on the activity of EL, LPL, PL and HL. Enzymes from HEK293/EL, LPL, and PL transfected cells were assayed using various concentrations of the above compounds. The data presented are the means of three experiments. The resulting $IC_{50}$s for EL, LPL, PL and HL are shown.

FIG. 4 provides a table that summarizes the potency and selectivity of selected compounds of the invention.

FIG. 6 schematically illustrates exemplary compounds of the invention.

FIG. 12 provides a table that demonstrates the selectivity of SBC-140,460, SBC-140,466 and SBC-140,472, which may be due to the presence of a 4-piperidine substituent on the sulphonamide ring.

DETAILED DESCRIPTION OF THE INVENTION

Figure 1:
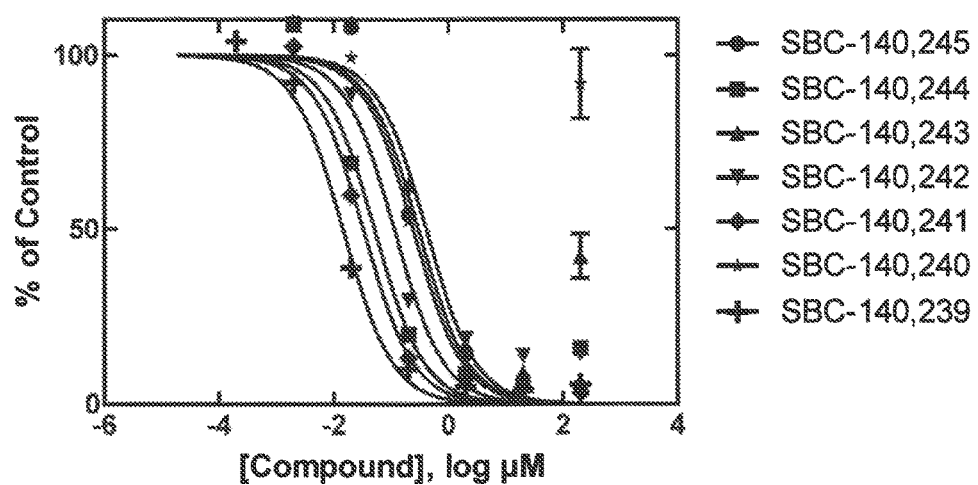
FIG. 1 graphically illustrates structure-activity relationship (SAR) data of several compounds of the invention, where cell extracts of HEK293/EL transfected cells were used for assaying the EL activities using various concentrations of each analog. The data presented are means of three experiments.

As previously noted, the present invention includes compounds of Formula I, Formula II, and variations thereof, and pharmaceutical compositions including such compounds. Moreover, the invention includes methods of using such compounds for treating various disorders and illnesses alleviated by inhibiting Endothelial Lipase (EL), or preventing or delaying the progression of those disorders and illnesses. More specifically, the present invention encompasses small molecule inhibitors of EL and may be used therapeutically to raise HDL-cholesterol levels in blood, and may be used in the prevention and/or treatment of cholesterol and lipoprotein metabolism disorders, including familial hypercholesterolemia, atherogenic dyslipidemia, atherosclerosis, and, more generally, cardiovascular disease (CVD).

HDL exerts several anti-atherosclerotic, anti-inflammatory and endothelial-protective effects. In particular, the promotion of reverse cholesterol transport as an anti-atherogenic effect of HDL may promote regression of atherosclerotic lesions. HDL may exert direct endothelial-protective effects and may stimulate endothelial repair processes. Although no formal National Cholesterol Education Program (NCEP) target treatment levels of HDL-C exist, an HDL level of <40 mg/dL is undesirable and measures should be taken to increase it. Furthermore, the prevalence of low levels of HDL-C (<40 mg/dL) is about 40%. The low level of HDL-C may be linked to poor CHD outcomes. Indeed, it is estimated that >40% of coronary events occur in individuals with HDL-C <40 mg/dL. These findings emphasize that the risk factor associated with a low level of HDL-C is independent of LDL-C. Thus, no matter how low the LDL-C level, a decrease in the HDL-C level increases the risk for coronary artery disease. Therefore, HDL elevation plays an important role in the prevention and treatment of atherosclerotic vascular disease.

Endothelial lipase (EL) is a member of the triglyceride (TG) lipase gene family. EL has both phospholipase and TG lipase activity, but it is more active as a phospholipase than as a TG lipase (phospholipase to TG lipase ratio, 1.6). There is a link between EL and HDL-C. HDL-C particles are the preferred source of EL substrate for all lipoprotein fractions. Furthermore, a significant increase in plasma HDL-C in mice was observed when the EL gene was knocked out. Using genetic mouse models with altered levels of EL expression, there is a strong inverse correlation between HDL levels and EL expression. Targeted EL deletion increases HDL particles with anti-inflammatory properties both in vitro and in vivo. And inhibition of EL activity in mice using an EL antibody may result in a significant increase in HDL-C. Conversely, overexpression of EL in transgenic animals results in a significant decrease in HDL-C. This suggests that EL, at least in mice, plays an important role in HDL-C metabolism. Further genetic association studies in humans demonstrated inverse correlations between EL and HDL-C levels.

The human EL is a protein of about 500 amino acids, with five potential N-glycosylation sites. The size of the expressed mature protein is 68 kDa. EL has 45%, 40%, and 27% amino acid sequence identity with lipoprotein lipase (LPL), hepatic lipase (HL) and pancreatic lipase (PL), respectively. The locations of the 10 cysteine residues, as well as the 19 amino acid lid region are conserved. The catalytic pocket of EL has the same conserved catalytic triad found in other members of the lipase family. The GXSXG lipase motif surrounding the active site serine is conserved. There are five possible heparin-binding consensus sequences in endothelial lipase, KLHKPK, RFKK, RKNR, KKMRNKR, and RRIRVK. In addition, there are two conserved potential lipid-binding domains (170-GLDPAGP-177) and (204-RSFGLSIGIQM-214).

Unlike LPL and HL, EL is synthesized by endothelial cells and functions at the site where it is synthesized. Furthermore, EL's tissue distribution is different from that of LPL and HL. As a lipase, EL has primarily phospholipase A1 activity, and it hydrolyzes effectively and specifically the HDL phospholipids in vitro and ex vivo. Animals that overexpress EL show reduced HDL cholesterol levels. Conversely, animals that are deficient in EL show a marked elevation in HDL cholesterol levels, suggesting that it plays a physiologic role in HDL metabolism. Unlike LPL and HL, EL is located in the vascular endothelial cells and its expression is highly regulated by cytokines and physical forces, indicating that it plays a role in the development of atherosclerosis.

The present invention meets the needs in the field by providing small molecule therapeutics that selectively inhibit EL for the treatment of CVD and related comorbidities.

As used herein, the term "halogen" shall mean chlorine, bromine, fluorine and iodine.

As used herein, unless otherwise noted, "alkyl" and "aliphatic" whether used alone or as part of a substituent group refers to straight and branched carbon chains having 1 to 20 carbon atoms or any number within this range, for example 1 to 6 carbon atoms or 1 to 4 carbon atoms. Designated numbers of carbon atoms (e.g. $C_1$-$C_6$) shall refer independently to the number of carbon atoms in an alkyl moiety or to the alkyl portion of a larger alkyl-containing substituent. Non-limiting examples of alkyl groups include methyl, ethyl, n-propyl, iso-propyl, n-butyl, sec-butyl, iso-butyl, tert-butyl, and the like. Alkyl groups can be optionally substituted. Non-limiting examples of substituted alkyl groups include hydroxymethyl, chloromethyl, trifluoromethyl, aminomethyl, 1-chloroethyl, 2-hydroxyethyl, 1,2-difluoroethyl, 3-carboxypropyl, and the like. In substituent groups with multiple alkyl groups such as ($C_1$-$C_6$ alkyl)$_2$amino, the alkyl groups may be the same or different.

As used herein, the terms "alkenyl" and "alkynyl" groups, whether used alone or as part of a substituent group, refer to straight and branched carbon chains having 2 or more carbon atoms, preferably 2 to 20, wherein an alkenyl chain has at least one double bond in the chain and an alkynyl chain has at least one triple bond in the chain. Alkenyl and alkynyl groups can be optionally substituted. Non-limiting examples of alkenyl groups include ethenyl, 3-propenyl, 1-propenyl (also 2-methylethenyl), isopropenyl (also 2-methylethen-2-yl), buten-4-yl, and the like. Nonlimiting examples of substituted alkenyl groups include 2-chloroethenyl (also 2-chlorovinyl), 4-hydroxybuten-1-yl, 7-hydroxy-7-methyloct-4-en-2-yl, 7-hydroxy-7-methyloct-3,5-dien-2-yl, and the like. Non-limiting examples of alkynyl groups include ethynyl, prop-2-ynyl (also propargyl), propyn-1-yl, and 2-methyl-hex-4-yn-1-yl. Non-limiting examples of substituted alkynyl groups include, 5-hydroxy-5-methylhex-3-ynyl, 6-hydroxy-6-methylhept-3-yn-2-yl, 5-hydroxy-5-ethylhept-3-ynyl, and the like.

As used herein, "cycloalkyl," whether used alone or as part of another group, refers to a non-aromatic carbon-containing ring including cyclized alkyl, alkenyl, and alkynyl groups, e.g., having from 3 to 14 ring carbon atoms, preferably from 3 to 7 or 3 to 6 ring carbon atoms, or even 3 to 4 ring carbon atoms, and optionally containing one or more (e.g., 1, 2, or 3) double or triple bond. Cycloalkyl groups can be monocyclic (e.g., cyclohexyl) or polycyclic (e.g., containing fused, bridged, and/or spiro ring systems), wherein the carbon atoms are located inside or outside of the ring system. Any suitable ring position of the cycloalkyl group can be covalently linked to the defined chemical structure. Cycloalkyl rings can be optionally substituted. Non-limiting examples of cycloalkyl groups include: cyclopropyl, 2-methyl-cyclopropyl, cyclopropenyl, cyclobutyl, 2,3-dihydroxycyclobutyl, cyclobutenyl, cyclopentyl, cyclopentenyl, cyclopentadienyl, cyclohexyl, cyclohexenyl, cycloheptyl, cyclooctanyl, decalinyl, 2,5-dimethylcyclopentyl, 3,5-dichlorocyclohexyl, 4-hydroxycyclohexyl, 3,3,5-trimethylcyclohex-1-yl, octahydropentalenyl, octahydro-1H-indenyl, 3a,4,5,6,7,7a-hexahydro-3H-inden-4-yl, decahydroazulenyl; bicyclo[6.2.0]decanyl, decahydronaphthalenyl, and dodecahydro-1H-fluorenyl. The term "cycloalkyl" also includes carbocyclic rings which are bicyclic hydrocarbon rings, non-limiting examples of which include, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

"Haloalkyl" is intended to include both branched and straight-chain saturated aliphatic hydrocarbon groups having the specified number of carbon atoms, substituted with 1 or more halogen. Haloalkyl groups include perhaloalkyl groups, wherein all hydrogens of an alkyl group have been replaced with halogens (e.g., —$CF_3$, $CF_2CF_3$). Haloalkyl groups can optionally be substituted with one or more substituents in addition to halogen. Examples of haloalkyl groups include, but are not limited to, fluoromethyl, dichloroethyl, trifluoromethyl, trichloromethyl, pentafluoroethyl, and pentachloroethyl groups.

The term "alkoxy" refers to the group —O-alkyl, wherein the alkyl group is as defined above. Alkoxy groups optionally may be substituted. The term $C_3$-$C_6$ cyclic alkoxy refers to a ring containing 3 to 6 carbon atoms and at least one oxygen atom (e.g., tetrahydrofuran, tetrahydro-2H-pyran). $C_3$-$C_6$ cyclic alkoxy groups optionally may be substituted.

The term "aryl," when used alone or as part of another group, is defined herein as an unsaturated, aromatic monocyclic ring of 6 carbon members or to an unsaturated, aromatic polycyclic ring of from 10 to 14 carbon members. Aryl rings can be, for example, a phenyl or naphthyl ring each optionally substituted with one or more moieties capable of replacing one or more hydrogen atoms. Non-limiting examples of aryl groups include: phenyl, naphthylen-1-yl, naphthylen-2-yl, 4-fluorophenyl, 2-hydroxyphenyl, 3-methylphenyl, 2-amino-4-fluorophenyl, 2-(N,N-diethylamino)phenyl, 2-cyanophenyl, 2,6-di-tert-butylphenyl, 3-methoxyphenyl, 8-hydroxynaphthylen-2-yl, 4,5-dimethoxynaphthylen-1-yl, and 6-cyano-naphthylen-1-yl. Aryl groups also include, for example, phenyl or naphthyl rings fused with one or more saturated or partially saturated carbon rings (e.g., bicyclo[4.2.0]octa-1,3,5-trienyl, indanyl), which can be substituted at one or more carbon atoms of the aromatic and/or saturated or partially saturated rings.

The term "arylalkyl" or "aralkyl" refers to the group -alkyl-aryl, where the alkyl and aryl groups are as defined herein. Aralkyl groups of the present invention are optionally substituted. Examples of arylalkyl groups include, for example, benzyl, 1-phenylethyl, 2-phenylethyl, 3-phenylpropyl, 2-phenylpropyl, fluorenylmethyl, diphenylmethyl and the like.

The terms "heterocyclic" and/or "heterocycle" and/or "heterocylyl," whether used alone or as part of another group, are defined herein as one or more ring having from 3 to 20 atoms wherein at least one atom in at least one ring is a heteroatom selected from nitrogen (N), oxygen (O), or sulfur (S), and wherein further the ring that includes the heteroatom is non-aromatic. In heterocycle groups that include 2 or more fused rings, the non-heteroatom bearing ring may be aryl (e.g., indolinyl, tetrahydroquinolinyl, chromanyl). Exemplary heterocycle groups have from 3 to 14 ring atoms of which from 1 to 5 are heteroatoms independently selected from nitrogen (N), oxygen (O), or sulfur (S). One or more N or S atoms in a heterocycle group can be oxidized. Heterocycle groups can be optionally substituted.

Non-limiting examples of heterocyclic units having a single ring include: diazirinyl, aziridinyl, urazolyl, azetidinyl, pyrazolidinyl, imidazolidinyl, oxazolidinyl, isoxazolinyl, isoxazolyl, thiazolidinyl, isothiazolyl, isothiazolinyloxathiazolidinonyl, oxazolidinonyl, hydantoinyl, tetrahydrofuranyl, pyrrolidinyl, morpholinyl, piperazinyl, piperidinyl, dihydropyranyl, tetrahydropyranyl, piperidin-2-onyl (valerolactam), 2,3,4,5-tetrahydro-1H-azepinyl, 2,3-dihydro-1H-indole, and 1,2,3,4-tetrahydro-quinoline. Non-limiting examples of heterocyclic units having 2 or more rings include: hexahydro-1H-pyrrolizinyl, 3a,4,5,6,7,7a-hexahydro-1H-benzo[d]imidazolyl, 3a,4,5,6,7,7a-hexahydro-1H-indolyl, 1,2,3,4-tetrahydroquinolinyl, chromanyl, isochromanyl, indolinyl, isoindolinyl, and decahydro-1H-cycloocta[b]pyrrolyl.

The term "heteroaryl," whether used alone or as part of another group, is defined herein as one or more rings having from 5 to 20 atoms wherein at least one atom in at least one ring is a heteroatom chosen from nitrogen (N), oxygen (O), or sulfur (S), and wherein further at least one of the rings that includes a heteroatom is aromatic. In heteroaryl groups that include 2 or more fused rings, the non-heteroatom bearing ring may be a carbocycle (e.g., 6,7-Dihydro-5H-cyclopentapyrimidine) or aryl (e.g., benzofuranyl, benzothiophenyl, indolyl). Exemplary heteroaryl groups have from 5 to 14 ring atoms and contain from 1 to 5 ring heteroatoms independently selected from nitrogen (N), oxygen (O), or sulfur (S). One or more N or S atoms in a heteroaryl group can be oxidized. Heteroaryl groups can be substituted. Non-limiting examples of heteroaryl rings containing a single ring include: 1,2,3,4-tetrazolyl, [1,2,3]triazolyl, [1,2,4]triazolyl, triazinyl, thiazolyl, 1H-imidazolyl, oxazolyl, furanyl, thiopheneyl, pyrimidinyl, 2-phenylpyrimidinyl, pyridinyl, 3-methylpyridinyl, and 4-dimethylaminopyridinyl. Non-limiting examples of heteroaryl rings containing 2 or more fused rings include: benzofuranyl, benzothiophenyl, benzoxazolyl, benzthiazolyl, benztriazolyl, cinnolinyl, naphthyridinyl, phenanthridinyl, 7H-purinyl, 9H-purinyl, 6-amino-9H-purinyl, 5H-pyrrolo[3,2-d]pyrimidinyl, 7H-pyrrolo[2,3-d]pyrimidinyl, pyrido[2,3-d]pyrimidinyl, 2-phenylbenzo[d]thiazolyl, 1H-indolyl, 4,5,6,7-tetrahydro-1-H-indolyl, quinoxalinyl, 5-methylquinoxalinyl, quinazolinyl, quinolinyl, 8-hydroxy-quinolinyl, and isoquinolinyl.

One non-limiting example of a heteroaryl group as described above is $C_1$-$C_5$ heteroaryl, which has 1 to 5 carbon ring atoms and at least one additional ring atom that is a heteroatom (preferably 1 to 4 additional ring atoms that are heteroatoms) independently selected from nitrogen (N), oxygen (O), or sulfur (S). Examples of C1-C5 heteroaryl include, but are not limited to, triazinyl, thiazol-2-yl, thiazol-4-yl, imidazol-1-yl, 1H-imidazol-2-yl, 1H-imidazol-4-yl, isoxazolin-5-yl, furan-2-yl, furan-3-yl, thiophen-2-yl, thiophen-4-yl, pyrimidin-2-yl, pyrimidin-4-yl, pyrimidin-5-yl, pyridin-2-yl, pyridin-3-yl, and pyridin-4-yl.

Unless otherwise noted, when two substituents are taken together to form a ring having a specified number of ring atoms (e.g., $R^2$ and $R^3$ taken together with the nitrogen (N) to which they are attached to form a ring having from 3 to 7 ring members), the ring can have carbon atoms and optionally one or more (e.g., 1 to 3) additional heteroatoms independently selected from nitrogen (N), oxygen (O), or sulfur (S). The ring can be saturated or partially saturated and can be optionally substituted.

For the purposes of the present invention, fused ring units, as well as spirocyclic rings, bicyclic rings and the like, which comprise a single heteroatom may be considered to belong to the cyclic family corresponding to the heteroatom containing ring. For example, 1,2,3,4-tetrahydroquinoline having the formula:

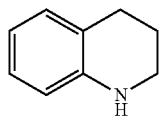

may be, for the purposes of the present invention, considered a heterocyclic unit. 6,7-Dihydro-5H-cyclopentapyrimidine having the formula:

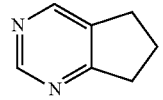

may be, for the purposes of the present invention, considered a heteroaryl unit. When a fused ring unit contains heteroatoms in both a saturated and an aryl ring, the aryl ring will predominate and determine the type of category to which the ring is assigned. For example, 1,2,3,4-tetrahydro-[1,8]naphthyridine having the formula:

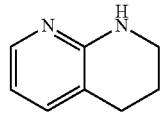

may be, for the purposes of the present invention, considered a heteroaryl unit.

Whenever a term or either of their prefix roots appear in a name of a substituent the name is to be interpreted as including those limitations provided herein. For example, whenever the term "alkyl" or "aryl" or either of their prefix roots appear in a name of a substituent (e.g., arylalkyl, alkylamino) the name may be interpreted as including those limitations given above for "alkyl" and "aryl."

The term "substituted" is used throughout the specification. The term "substituted" may be defined herein as a moiety, whether acyclic or cyclic, which has one or more hydrogen atoms replaced by a substituent or several (e.g., 1 to 10) substituents as defined herein below. The substituents are capable of replacing one or two hydrogen atoms of a single moiety at a time. In addition, these substituents can replace two hydrogen atoms on two adjacent carbons to form said substituent, new moiety or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. The term "substituted" may be used to indicate that a moiety can have one or more of the hydrogen atoms replaced by a substituent. When a moiety is described as "substituted" any number of the hydrogen atoms may be replaced. For example, difluoromethyl is a substituted $C_1$ alkyl; trifluoromethyl is a substituted $C_1$ alkyl; 4-hydroxyphenyl is a substituted aromatic ring; (N,N-dimethyl-5-amino)octanyl is a substituted $C_8$ alkyl; 3-guanidinopropyl is a substituted $C_3$ alkyl; and 2-carboxypyridinyl is a substituted heteroaryl.

The variable groups defined herein, e.g., alkyl, alkenyl, alkynyl, cycloalkyl, alkoxy, aryloxy, aryl, heterocycle and heteroaryl groups defined herein, whether used alone or as part of another group, may be optionally substituted. Optionally substituted groups may be so indicated.

The following are non-limiting examples of substituents that may substitute for hydrogen atoms on a moiety: halogen (chlorine (Cl), bromine (Br), fluorine (F) and iodine(I)), —CN, —NO$_2$, oxo (=O), —OR$^4$, —SR$^4$, —N(R$^4$)$_2$, —NR$^4$C(O)R$^4$, —SO$_2$R$^4$, —SO$_2$OR$^4$, —SO$_2$N(R$^4$)$_2$, —C(O)R$^4$, —C(O)OR$^4$, —C(O)N(R$^4$)$_2$, $C_{1-6}$ alkyl, $C_{1-6}$ haloalkyl, $C_1$-$C_6$ alkoxy, $C_2$-$C_8$ alkenyl, $C_2$-$C_8$ alkynyl, $C_3$-$C_{14}$ cycloalkyl, aryl, heterocycle, or heteroaryl, wherein each of the alkyl, haloalkyl, alkenyl, alkynyl, alkoxy, cycloalkyl, aryl, heterocycle, and heteroaryl groups is optionally substituted with 1-10 (e.g., 1-6 or 1-4) groups selected independently from halogen, —CN, —NO$_2$, oxo, and R$^4$; wherein R$^4$, at each occurrence, independently is hydrogen, —OR$^5$, —SR$^5$, —C(O)R$^5$, —C(O)OR$^5$, —C(O)N(R$^5$)$_2$, —SO$_2$R$^5$, S(O)$_2$OR$^5$, —N(R$^5$)$_2$, —NR$^5$C(O)R$^5$, $C_1$-$C_6$ alkyl, $C_1$-$C_6$ haloalkyl, $C_2$-$C_8$ alkenyl, $C_2$-$C_8$ alkynyl, cycloalkyl (e.g., $C_3$-$C_6$ cycloalkyl), aryl, heterocycle, or heteroaryl, or two R$^4$ units taken together with the atom(s) to which they are bound form an optionally substituted carbocycle or heterocycle wherein said carbocycle or heterocycle has 3 to 7 ring atoms; wherein R$^5$, at each occurrence, independently is hydrogen, $C_1$-$C_6$ alkyl, $C_1$-$C_6$ haloalkyl, $C_2$-$C_8$ alkenyl, $C_2$-$C_8$ alkynyl, cycloalkyl (e.g., $C_3$-$C_6$ cycloalkyl), aryl, heterocycle, or heteroaryl, or two R$^5$ units taken together with the atom(s) to which they are bound form an optionally substituted carbocycle or heterocycle wherein said carbocycle or heterocycle preferably has 3 to 7 ring atoms.

In some embodiments, the substituents that may substitute for hydrogen atoms on a moiety may be selected from
  i) —OR$^6$; for example, —OH, —OCH$_3$, —OCH$_2$CH$_3$, —OCH$_2$CH$_2$CH$_3$;
  ii) —C(O)R$^6$; for example, —COCH$_3$, —COCH$_2$CH$_3$, —COCH$_2$CH$_2$CH$_3$;
  iii) —C(O)OR$^6$; for example, —CO$_2$CH$_3$, —CO$_2$CH$_2$CH$_3$, —CO$_2$CH$_2$CH$_2$CH$_3$;
  iv) —C(O)N(R$^6$)$_2$; for example, —CONH$_2$, —CONHCH$_3$, —CON(CH$_3$)$_2$;
  v) —N(R$^6$)$_2$; for example, —NH$_2$, —NHCH$_3$, —N(CH$_3$)$_2$, —NH(CH$_2$CH$_3$);
  vi) Halogen: —F, —Cl, —Br, and —I;
  vii) —CH$_m$X$_n$; wherein X is halogen, m is from 0 to 2, m+n=3; for example, —CH$_2$F, —CHF$_2$, —CF$_3$, —CCl$_3$, or —CBr$_3$;
  viii) —SO$_2$R$^6$; for example, —SO$_2$H; —SO$_2$CH$_3$; —SO$_2$C$_6$H$_5$;
  ix) $C_1$-$C_6$ linear, branched, or cyclic alkyl;
  x) Cyano;
  xi) Nitro;
  xii) N(R$^6$)C(O)R$^6$;
  xiii) Oxo (=O);
  xiv) Heterocycle; and
  xv) Heteroaryl.
wherein each R$^6$ may independently be hydrogen, optionally substituted $C_1$-$C_6$ linear or branched alkyl (e.g., optionally substituted $C_1$-$C_4$ linear or branched alkyl), or optionally substituted $C_3$-$C_6$ cycloalkyl (e.g optionally substituted $C_3$-$C_4$ cycloalkyl); or two R$^6$ units can be taken together to form a ring comprising 3-7 ring atoms. In certain aspects, each R$^6$ is independently hydrogen, $C_1$-$C_6$ linear or branched alkyl optionally substituted with halogen or $C_3$-$C_6$ cycloalkyl.

For example, at various places in the present specification, substituents of compounds are disclosed in groups or in ranges. It is specifically intended that the description include each and every individual subcombination of the members of such groups and ranges. For example, the term "$C_1$-$C_6$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl.

All stereoisomers of the compounds described herein, either in a mixture or in pure or substantially pure form, are considered to be within the scope of this invention. The compounds of the present invention can have asymmetric centers at any of the carbon atoms including any one of the R substituents. Consequently, compounds used in the method of the invention can exist in enantiomeric or diastereomeric forms or in mixtures thereof. The processes for preparation of such compounds can utilize racemates, enantiomers or diastereomers as starting materials. When diastereomeric or enantiomeric products are prepared, they can be separated by conventional methods for example, chromatographic, chiral HPLC or fractional crystallization.

In addition to the compounds described herein (i.e., EL inhibitors), the present invention provides methods for the treatment or prophylaxis of cholesterol and lipoprotein metabolism disorders, including low HDL "good" cholesterol, familial hypercholesterolemia, atherogenic dyslipidemia, atherosclerosis, and, more generally, cardiovascular disease (CVD) in a patient in need of such treatment, which includes administering to such patient a therapeutically effective amount of an EL inhibitor of the invention. EL inhibitors used in the methods of the invention may have the general Formula (I), above.

In certain other embodiments, the EL inhibitors used in the methods of the invention may have the general Formula (I), wherein m+n=3-5 and/or R$^3$ includes at least one of an optionally substituted aryl and aralkyl. In further embodiments, the EL inhibitors used in the methods of the invention may have the general Formula (II).

As used herein, the expression "method of treating disease alleviated by endothelial lipase (EL) inhibitors" refers to a treatment using one or more of the compounds described herein, which provides relief either by freeing the recipient of a disease or condition mediated by EL or easing the symptoms or effects of such disease or condition. The methods of the invention are intended for treating, preventing, managing, and/or delaying the progression of the following: dyslipidemia, low HDL cholesterol, atherosclerosis, CVD, and/or coronary heart disease. The diseases and conditions enumerated above are given by way of example and not by way of limitation. In a preferred aspect, the invention provides a method for treating or preventing at least one symptom of dyslipidemia, hypercholesterolemia, atherosclerosis, CVD, and/or coronary heart disease, in a patient comprising administering to the individual an effective amount of an EL inhibitor.

Certain EL inhibitors of the invention include those compounds set forth in FIGS. 6 to 9. The EL inhibitors of the invention may, in certain embodiments, include those compounds set forth in FIG. 7, FIG. 8, and/or FIG. 9. Additionally, in a particularly preferred embodiment, the EL inhibitor of the invention may be SBC-140,239, set forth in FIG. 9.

As used herein, the terms "patient" or "subject" may be used interchangeably and may include both humans and animals.

The compounds used in the method of the invention may be administered as salts, which are also within the scope of this invention. Pharmaceutically acceptable (i.e., non-toxic, physiologically compatible) salts are preferred. If the compounds of the invention have, for example, at least one basic center, they can form acid addition salts. These may be formed, for example, with strong inorganic acids, such as mineral acids, for example sulfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, for example aspartic or glutamic acid or lysine or arginine, or benzoic acid, or with organic sulfonic acids, such as ($C_1$-$C_4$) alkyl or arylsulfonic acids which are unsubstituted or substituted, for example by halogen, for example methyl- or para-toluenesulfonic acid. Corresponding acid addition salts can also be formed having plural basic centers, if desired. The compounds used in the method of the present invention having at least one acid group (e.g., COOH) can also form salts with suitable bases. Representative examples of such salts include metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or tri-lower alkylamine, for example ethyl, tert-butyl, diethyl, diisopropyl, triethyl, tributyl or dimethylpropylamine, or a mono, di or trihydroxy lower alkylamine, for example mono, di or triethanolamine. Corresponding internal salts may also be formed.

The pharmaceutically acceptable salts of compounds of the present invention can also exist as various solvates, such as, for example, with water (i.e., a hydrate), methanol, ethanol, dimethylformamide, ethyl acetate. Solvate mixtures may also be prepared in accordance with the present invention. The source of such solvates may be from the solvent of crystallization, inherent in the solvent of preparation or crystallization, or adventitious to such solvent. Solvates and hydrates are within the scope of the present invention.

Biological data derived from testing compounds of the invention and/or treating patients with compounds of the invention may be used to develop models and, for example, a drug or therapeutic pharmacophore model to allow for the development of additional active compounds or agents. As used herein, the term "pharmacophore" refers to the ensemble of steric and electronic features that are necessary to ensure the optimal supramolecular interactions with a specific biological target structure and to trigger, activate, block, inhibit or modulate the biological target's biological activity, as the case may be. See, IUPAC, *Pure and Applied Chemistry* (1998) 70:1129-1143.

In carrying out the methods of the invention, the above-described compounds may be administered as such, or in a form from which the active agent can be derived, such as a prodrug. A prodrug is a derivative of a compound described herein, the pharmacologic action of which results from the conversion by chemical or metabolic processes in vivo to the active compound. The term "prodrug esters" as employed herein includes esters and carbonates formed by reacting one or more hydroxyls of compounds used in the method of the invention with alkyl, alkoxy, or aryl substituted acylating agents employing procedures known to those skilled in the art to generate acetates, pivalates, methylcarbonates, benzoates and the like. Any compound that can be converted in vivo to provide the bioactive agent (i.e., a compound of formula I) is a prodrug within the scope and spirit of the invention. Various forms of prodrugs are well known in the art. A comprehensive description of prodrugs and prodrug derivatives are described in: (a) The Practice of Medicinal Chemistry, Camille G. Wermuth et al., Ch 31, (Academic Press, 1996); (b) Design of Prodrugs, edited by H. Bundgaard, (Elsevier, 1985); (c) A Textbook of Drug Design and Development, P. Krogsgaard-Larson and H. Bundgaard, eds., Ch. 5, pp., 113-191 (Harwood Academic Publishers, 1991).

The terms "administer", "administration" or "administering" as used herein refer to (1) providing, giving, dosing and/or prescribing by either a health practitioner or his authorized agent or under his direction a compound according to this invention, and (2) putting into, taking or consuming by the patient or person himself or herself, a compound according to this invention.

The agents or compounds used in practicing the methods of the invention may be administered in an amount sufficient to induce the desired therapeutic effect in the recipient thereof. Thus the term "therapeutically effective amount" as used herein refers to an amount of a therapeutic agent which is sufficient to treat or prevent a condition treatable by administration of one or more of the compounds of the invention, above, or a prodrug thereof. Preferably, the therapeutically effective amount refers to the amount of a compound of the invention appropriate to treat an EL-associated condition, i.e. to bring about a detectable therapeutic or preventative or ameliorative effect. The effect may include, for example, treatment or prevention of the conditions described herein.

The compound(s) described herein may be administered at a dose in range from about 0.01 mg to about 200 mg/kg of body weight per day. A dose of from 0.1 to 100, and preferably from 1 to 30 mg/kg per day in one or more applications per day should be effective to produce the desired result. By way of example, a suitable dose for oral administration would be in the range of 1-30 mg/kg of body weight per day, whereas a typical dose for intravenous administration would be in the range of 1-10 mg/kg of body weight per day. Of course, as those skilled in the art will appreciate, the dosage actually administered will depend upon the condition being treated, the age, health and weight of the recipient, the type of concurrent treatment, if any, and the frequency of treatment. Moreover, the effective dosage amount may be determined by one skilled in the art on the basis of routine empirical activity testing to measure the bioactivity of the compound(s) in a bioassay, and thus establish the appropriate dosage to be administered.

The compounds used in the methods of the invention may typically be administered from 1-4 times a day, so as to deliver the above-mentioned daily dosage. However, the exact regimen for administration of the compounds described herein will necessarily be dependent on the needs of the individual subject being treated, the type of treatment administered and the judgment of the attending medical specialist.

In general, the compound(s) used in the method of the invention can be administered to achieve EL inhibition by using any acceptable route known in the art, either alone or in combination with one or more other therapeutic agents. Thus, the active agent(s) can be administered orally, buccally, parenterally, such as by intravenous or intra-arterial infusion, intramuscular, intraperitoneal, intrathecal or subcutaneous injection, by liposome-mediated delivery, rectally, vaginally, by inhalation or insufflation, transdermally or by otic delivery.

The orally administered dosage unit may be in the form of tablets, caplets, dragees, pills, semisolids, soft or hard gelatin capsules, aqueous or oily solutions, emulsions, suspensions or syrups. Suitable dosage forms for parenteral administration include injectable solutions or suspensions, suppositories, powder formulations, such as microcrystals or aerosol spray. The active agent may also be incorporated into a conventional transdermal delivery system.

As used herein, the expression "pharmaceutically acceptable carrier medium" includes any and all solvents, diluents, or other liquid vehicle, dispersion or suspension aids, surface agent agents, isotonic agents, thickening or emulsifying agents, preservatives, solid binders, lubricants, fillers and the like as suited for the particular dosage form desired. Remington: The Science and Practice of Pharmacy, 20th edition, (A. R. Genaro et al., Part 5, Pharmaceutical Manufacturing, pp. 669-1015 (Lippincott Williams & Wilkins, Baltimore, Md./Philadelphia, Pa.) (2000)) discloses various carriers used in formulating pharmaceutical compositions and known techniques for the preparation thereof. Except insofar as any conventional pharmaceutical carrier medium is incompatible with the EL inhibitors of the present invention, such as by producing an undesirable biological effect or otherwise interacting in a deleterious manner with any other component(s) of a formulation comprising such compounds, its use is contemplated to be within the scope of this invention. The compound(s) of the invention may be administered either simultaneously (e.g., in the same formulation or not) or sequentially with the supplemental therapeutic agent(s).

A pharmaceutical composition in accordance with the present invention includes one or more of the compounds as set forth herein in combination or admixture with a pharmaceutically acceptable carrier medium.

For the production of solid dosage forms, including hard and soft capsules, a therapeutic agent or compound of the invention may be mixed with pharmaceutically inert, inorganic or organic excipients, such as lactose, sucrose, glucose, gelatine, malt, silica gel, starch or derivatives thereof, talc, stearic acid or its salts, dried skim milk, vegetable, petroleum, animal or synthetic oils, wax, fat, polyols, and the like. For the production of liquid solutions, emulsions or suspensions or syrups one may use excipients such as water, alcohols, aqueous saline, aqueous dextrose, polyols, glycerine, lipids, phospholipids, cyclodextrins, vegetable, petroleum, animal or synthetic oils. For suppositories one may use excipients, such as vegetable, petroleum, animal or synthetic oils, wax, fat and polyols. For aerosol formulations, one may use compressed gases suitable for this purpose, such as oxygen, nitrogen and carbon dioxide. The pharmaceutical composition or formulation may also contain one or more additives including, without limitation, preservatives, stabilizers, e.g., UV stabilizers, emulsifiers, sweeteners, salts to adjust the osmotic pressure, buffers, coating materials and antioxidants.

The present invention further includes controlled-release, sustained-release, or extended-release therapeutic dosage forms for administration of a therapeutic agent or compound of the invention, which involves incorporation of the active agent into a suitable delivery system. This dosage form controls release of the therapeutic agent(s) in such a manner that an effective concentration of the therapeutic agent(s) in the bloodstream may be maintained over an extended period of time, with the concentration in the blood remaining relatively constant, to improve therapeutic results and/or minimize side effects. Additionally, a controlled-release system would provide minimum peak to trough fluctuations in blood plasma levels of the therapeutic agent.

In pharmaceutical compositions used in practicing the methods of the invention, the therapeutic agent(s) may be present in an amount of at least 0.5 and generally not more than 95% by weight, based on the total weight of the composition, including carrier medium and/or supplemental active agent(s), if any. Preferably, the proportion of active agent(s) varies between 30-90% by weight of the composition.

The preferred compounds for use in practicing the methods of the invention include those of Formulas I and II, and the variations described herein. In certain aspects, the compounds used in practicing the methods of the invention are those selected from Formula II.

In certain embodiments, the compounds used in practicing the methods of the invention may include one or more of the compounds set forth in FIGS. 6 to 9. However, in certain embodiments, the compounds used in practicing the methods of the invention may include one or more of the compounds set forth in FIGS. 7 to 9.

The methods of the present invention will normally include medical follow-up to determine the therapeutic or prophylactic effect brought about in the subject undergoing treatment with the compound(s) and/or composition(s) described herein.

The following examples describe the invention in further detail. These examples are provided for illustrative purposes only, and should in no way be considered as limiting the invention.

EXAMPLES

Example 1: Test for EL Inhibition

Assay Development: We developed and implemented a sensitive and robust assay for EL compound screening as well as assays for validation of compound selectivity.

Preparation of constructs: We have cloned the human full-length EL, LPL, HL and PL. The cDNA encoding the EL, LPL, HL and PL sequence was cloned by PCR and subcloned into a mammalian expression vector containing the cytomegalovirus promoter-enhancer. The constructs were confirmed by sequence analysis.

Expression of EL, LPL, HL and PL in mammalian cells: The above constructs were used to transfect HEK-293 cells. The cells were seeded into T75 plates in a DMEM solution containing 10% Fetal Bovine Serum media and incubated overnight at 37° C. Cells were transiently transfected with various cDNA constructs using the Lipofectamine-LTX as described by the manufacturer (Invitrogen). After transfection, cells were then incubated for an additional 48 hours at 37° C. before being analyzed for expression. After 48 hours of incubation, following transfection, cells were collected for analysis by western blots for the expression of EL, LPL, HL and PL.

EL screening assay: We developed and implemented two assays (a) in assay one the HDL-C functions as a substrate for the assay. This assay measures the rate of HDL hydrolysis by EL that yields free fatty acids, which are then coupled through acyl-CoA synthetase, acyl-CoA oxidase and horseradish peroxidase to produce the fluorescent species, resorufin; (b) in assay two PED-A1, a novel fluorogenic phospholipase A1-selective substrate was used for EL measurements. Testing using assay two revealed that it is more specific and robust. Assay one was used for initial screening, while assay two was used for secondary screening and EL kinetics.

LPL, PL and HL selectivity assays: For measuring LPL, PL and HL activity, we used the commercially available phospholipase kit (MGT). The activity of the substrate, resorufinoleate is quite good for both phospholipase A1 and phospholipase A2, and therefore is ideal for LPL, PL and HL. Since the substrate is quite general for other lipases such as triacylglycerol lipases or lipoprotein lipases, we utilized our recombinant system and cell specific expression system to achieve the desired specificity. The LPL, PL and HL enzyme activity measurements were conducted using a 96-well microtiter plate. All appropriate controls were implemented.

Characterization of the Hits: A library of compounds that modified both the urea and sulfonamide substituents on the 5-methyl furan were synthesized. The library was extensively analyzed for EL potency, and then the data was utilized to further optimize the compounds. Seven compounds were selected for potency, kinetic and selectivity confirmation. Data in FIG. 1 shows their effect on EL activity using various concentrations of selected EL compounds. The data in FIG. 4 shows these and related compounds exhibited a concentration dependent inhibition of EL activity with $IC_{50}$s ranging from low nM to low µM.

Figure 2A:
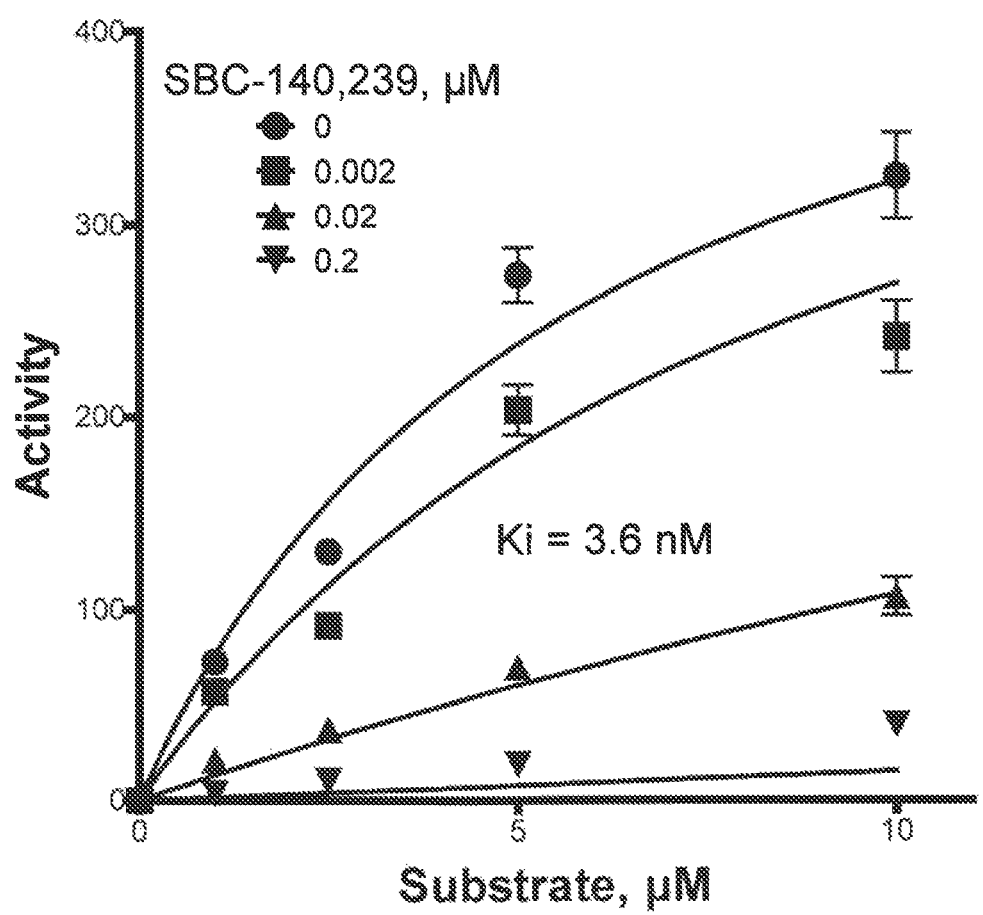
FIGS. 2A to 2C graphically illustrate the inhibition of EL by SBC-140,239 (FIG. 2A), SBC-140,241 (FIG. 2B) and SBC-140,244 (FIG. 2C). Enzyme from HEK293/EL transfected cells was used to determine the Ki using different concentrations of both substrate and inhibitors. The Ki was determined to be in agreement with the $IC_{50}$ values shown in FIG. 1.
Figure 2B:
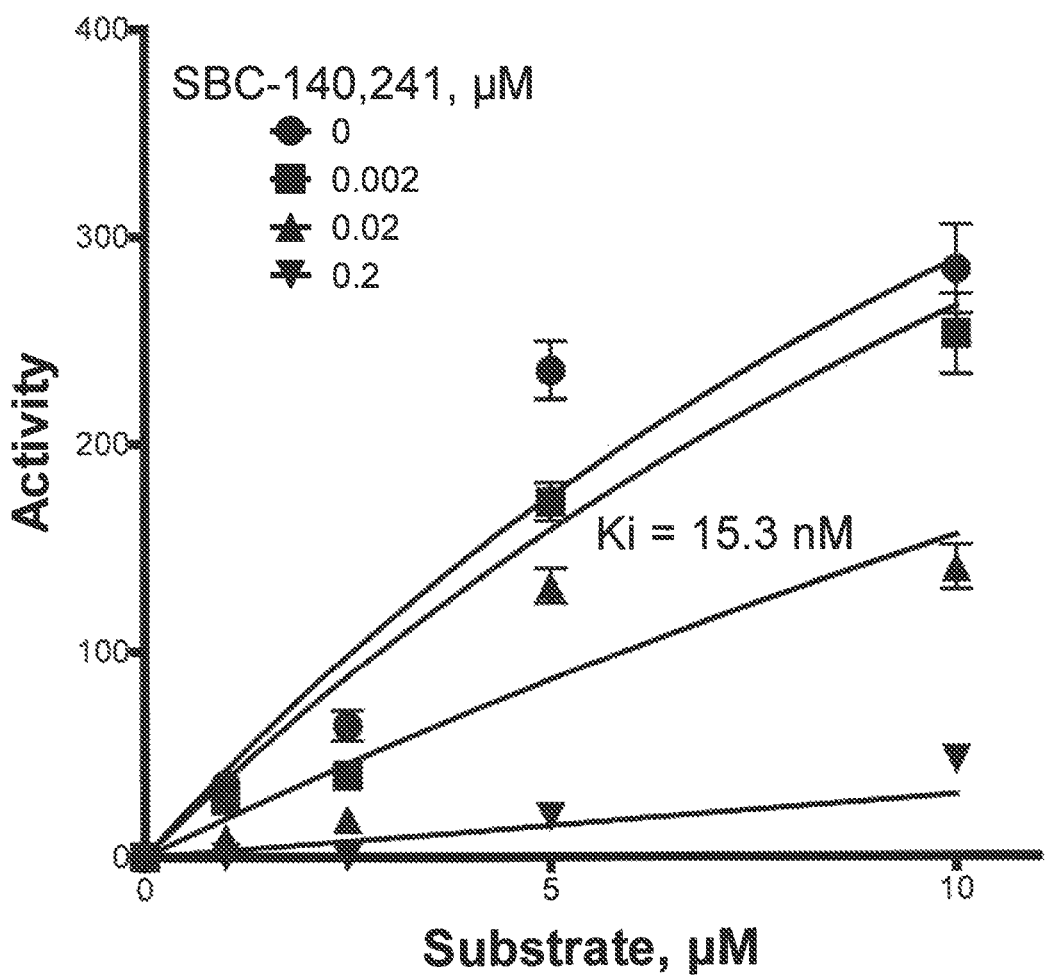
Figure 2C:
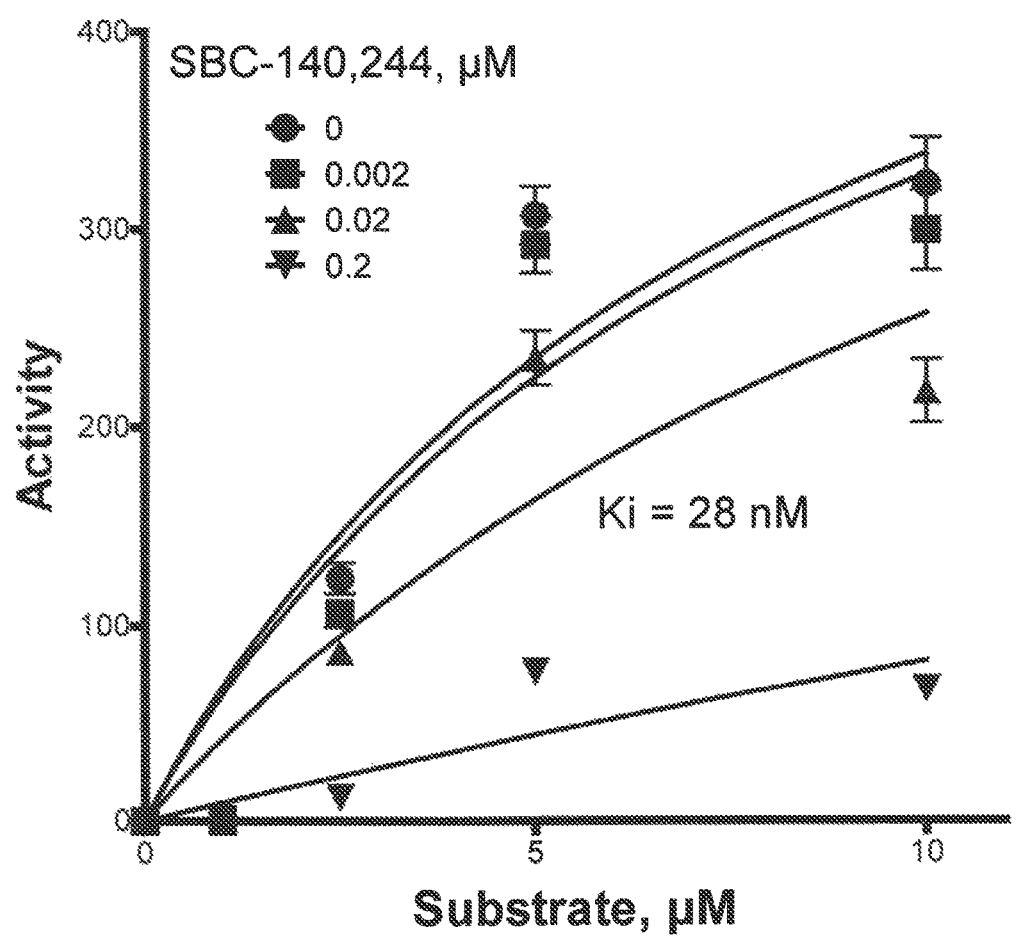

In order to determine the Ki value, we used variable concentrations of the compound and variable substrate concentrations. The Ki of selected compounds was determined to be in agreement with the $IC_{50}$ values (FIG. 2).

Example 2: Test for Inhibitor Selectivity

Experiments were also performed to determine the specificity of our best compounds against the most closely related homologues, LPL, PL and HL. Dose response curves for these compounds against EL, PL, LPL and HL are shown in FIG. 3.

In summary, we have identified several potent and selective compounds (FIG. 4). These are novel, structurally distinct EL inhibitors with potency in the low nM range that exhibit >100-fold selectivity against PL, LPL and HL.

Example 3: General Procedures for Synthesis of Compounds of the Formula I

Figure 5:
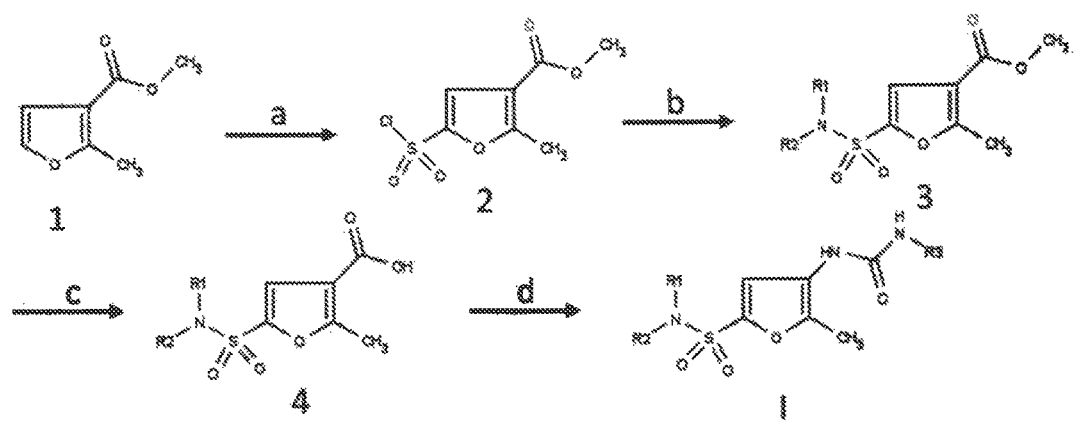
FIG. 5 schematically illustrates an exemplary synthetic procedure to make compounds of Formula I. A general synthetic route to make exemplary compounds of the invention (I), including the steps of: (a) $ClSO_2OH$, DCM, then pyridine, $PCl_5$; (b) $R^1R^2NH$, $Et_3N$, DCM; (c) NaOH, MeOH; (d) DPPA, $Et_3N$, toluene, then $R^3R^4NH$.
Figure 7:
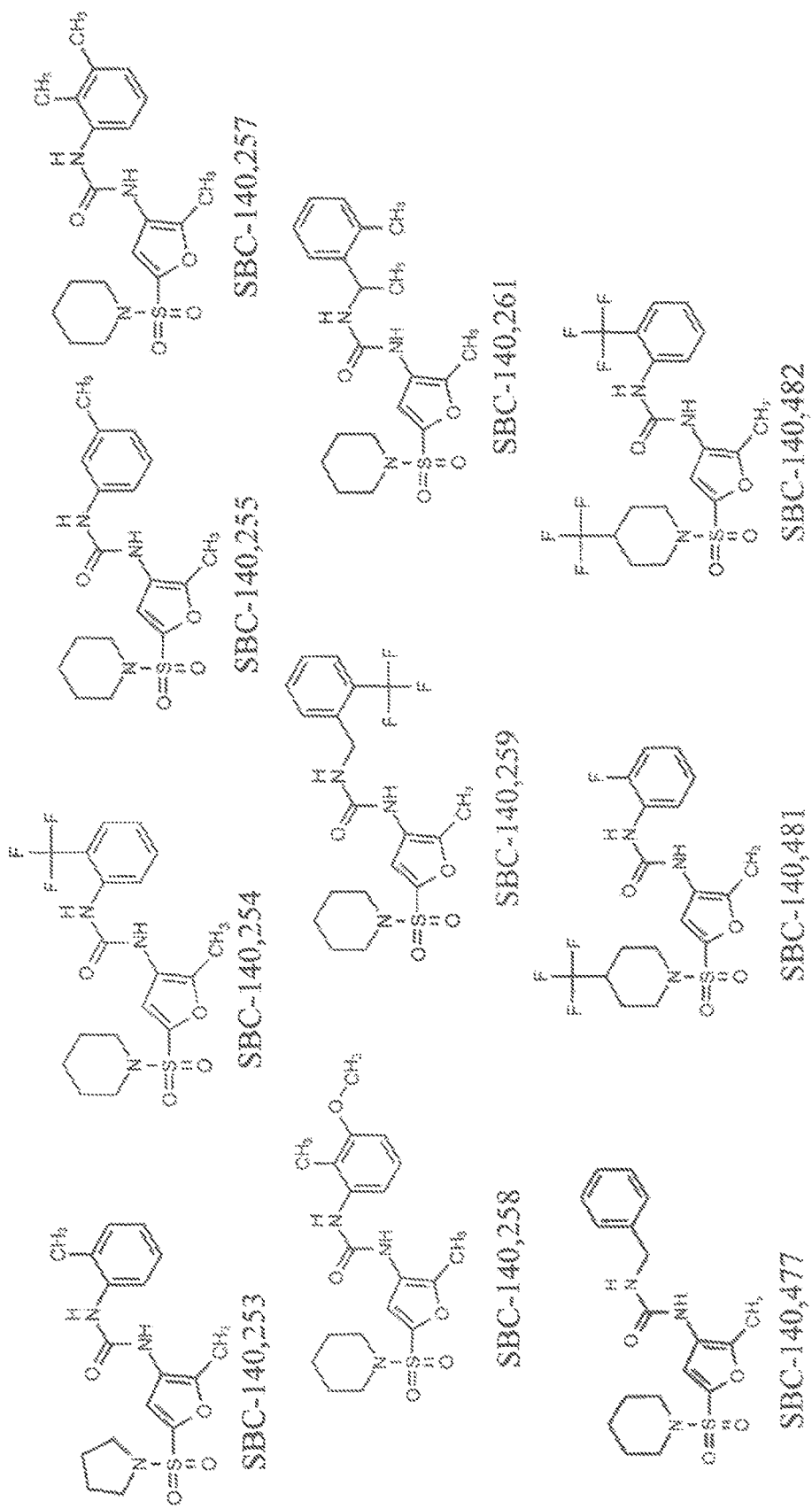
FIG. 7 schematically illustrates certain compounds of the invention having an EL $IC_{50}$ greater than 10 μM.
Figure 8:
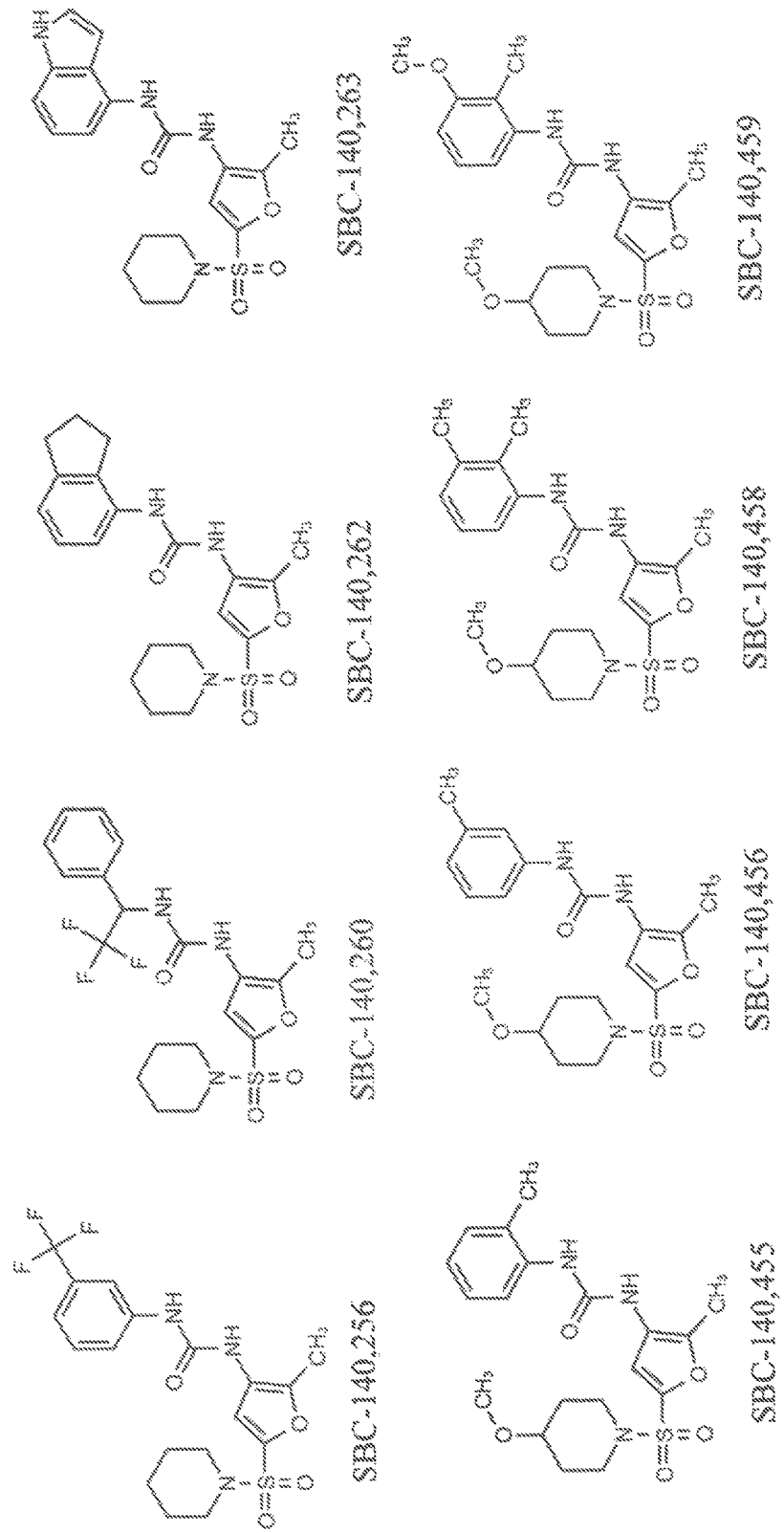
FIG. 8 schematically illustrates certain compounds of the invention having an EL $IC_{50}$ between 0.5 and 10 μM.
Figure 8:
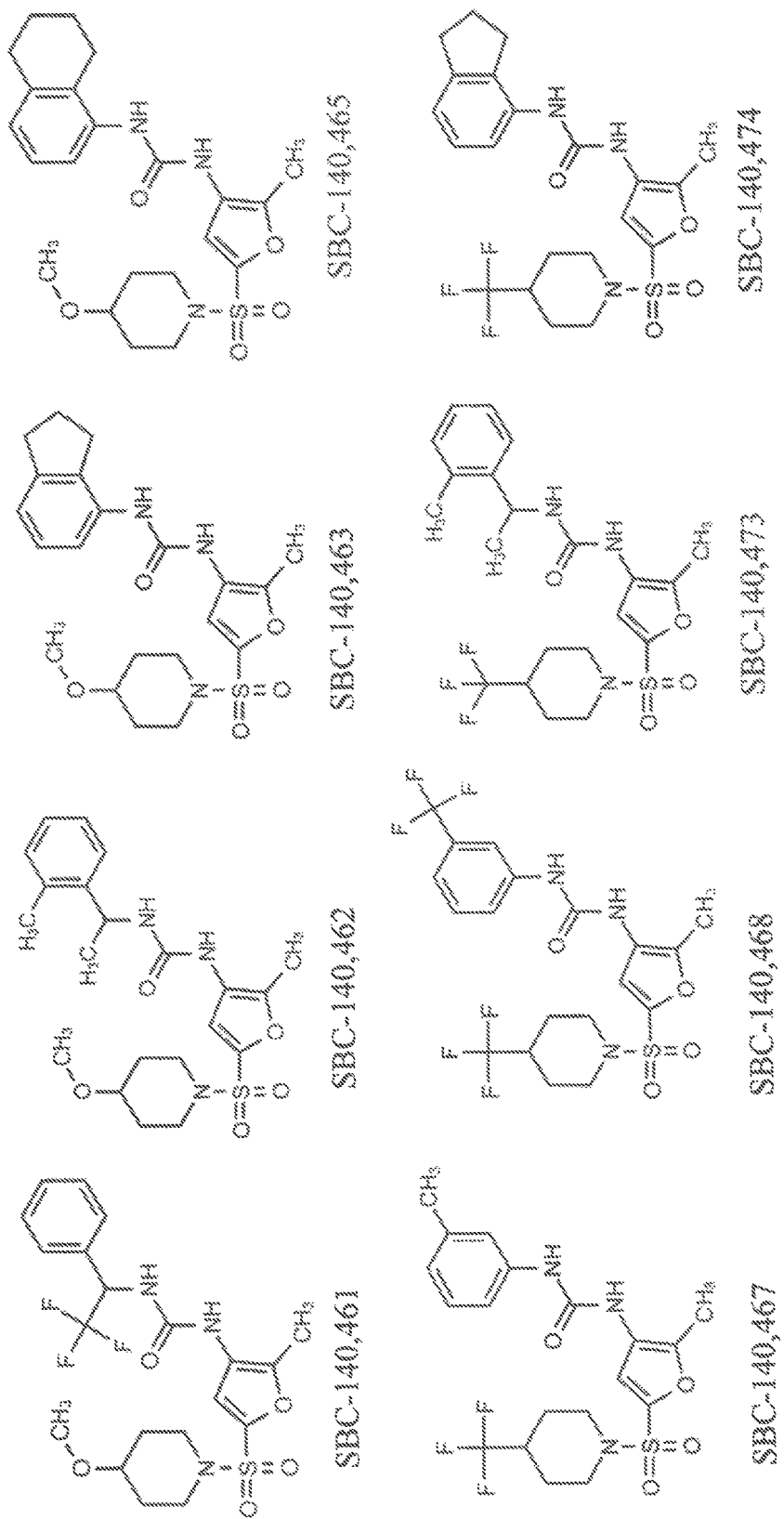
Figure 8:
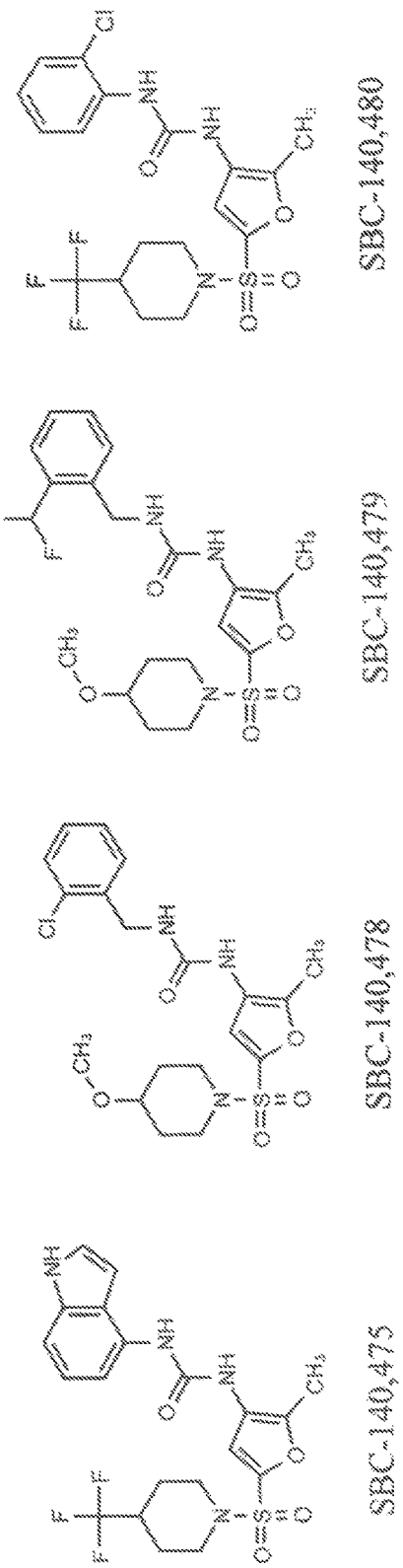
Figure 9:
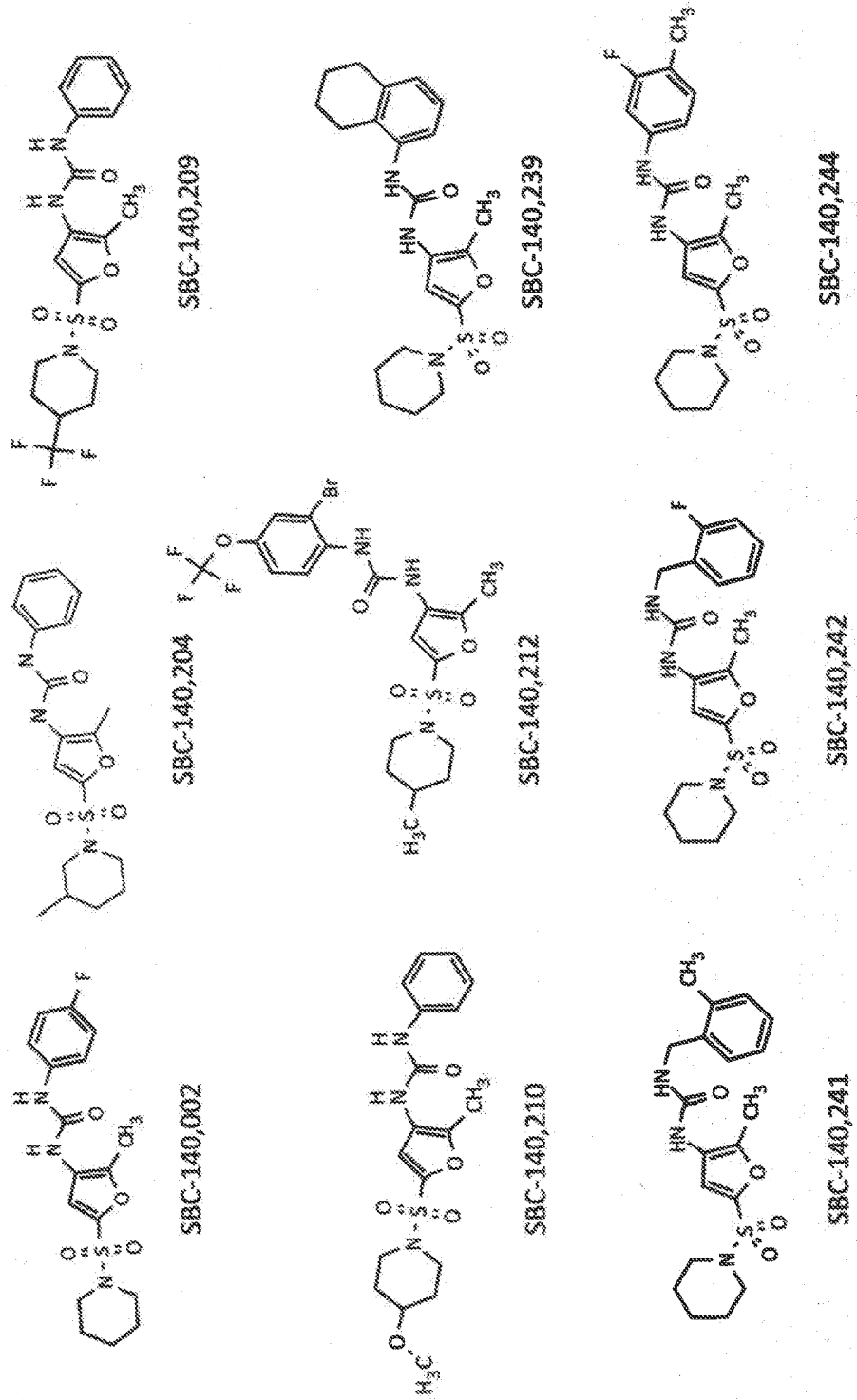
FIG. 9 schematically illustrates certain compounds of the invention having an EL IC$_{50}$ that is less than 0.5 µM.
Figure 9:
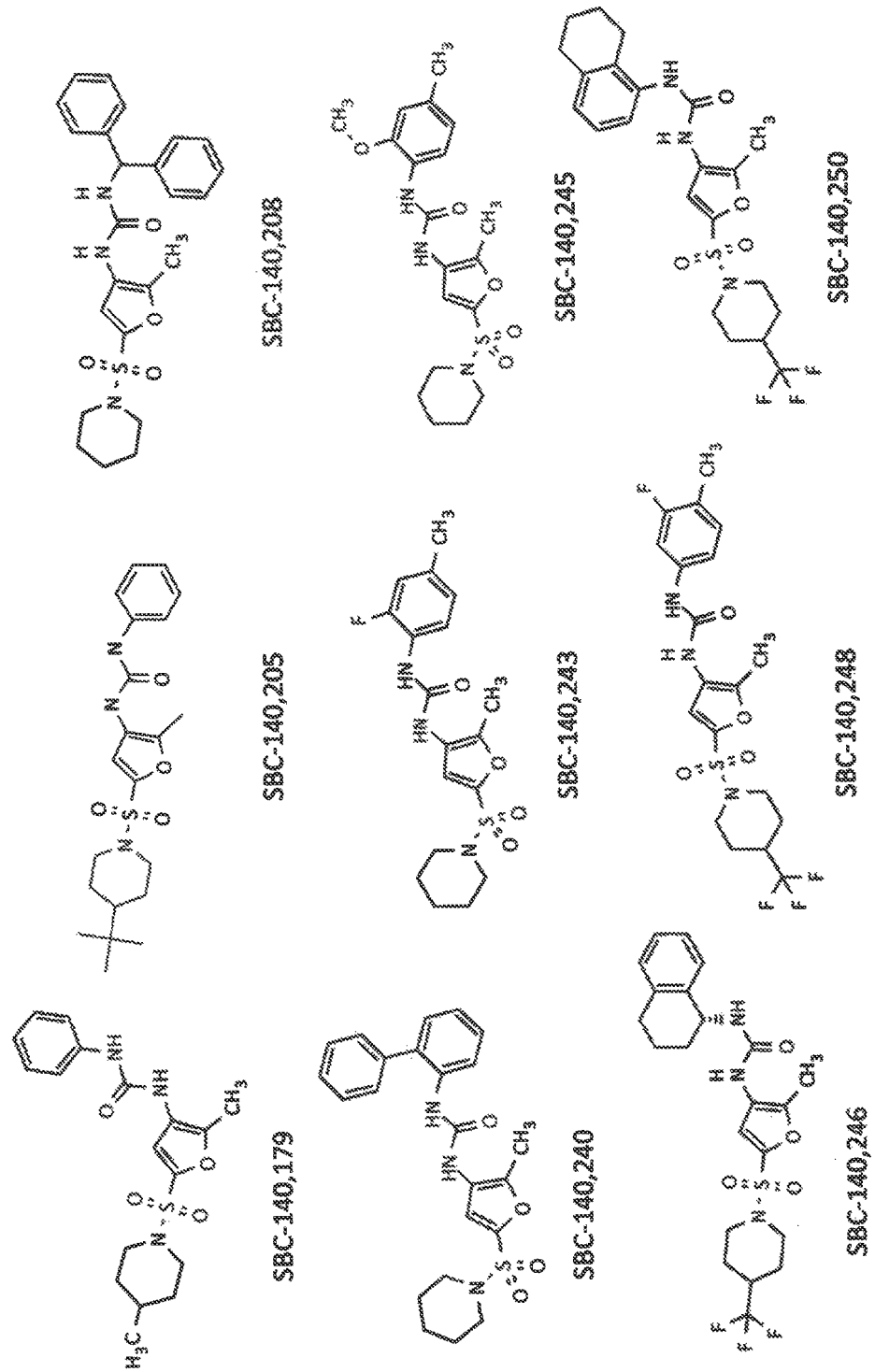
Figure 9:
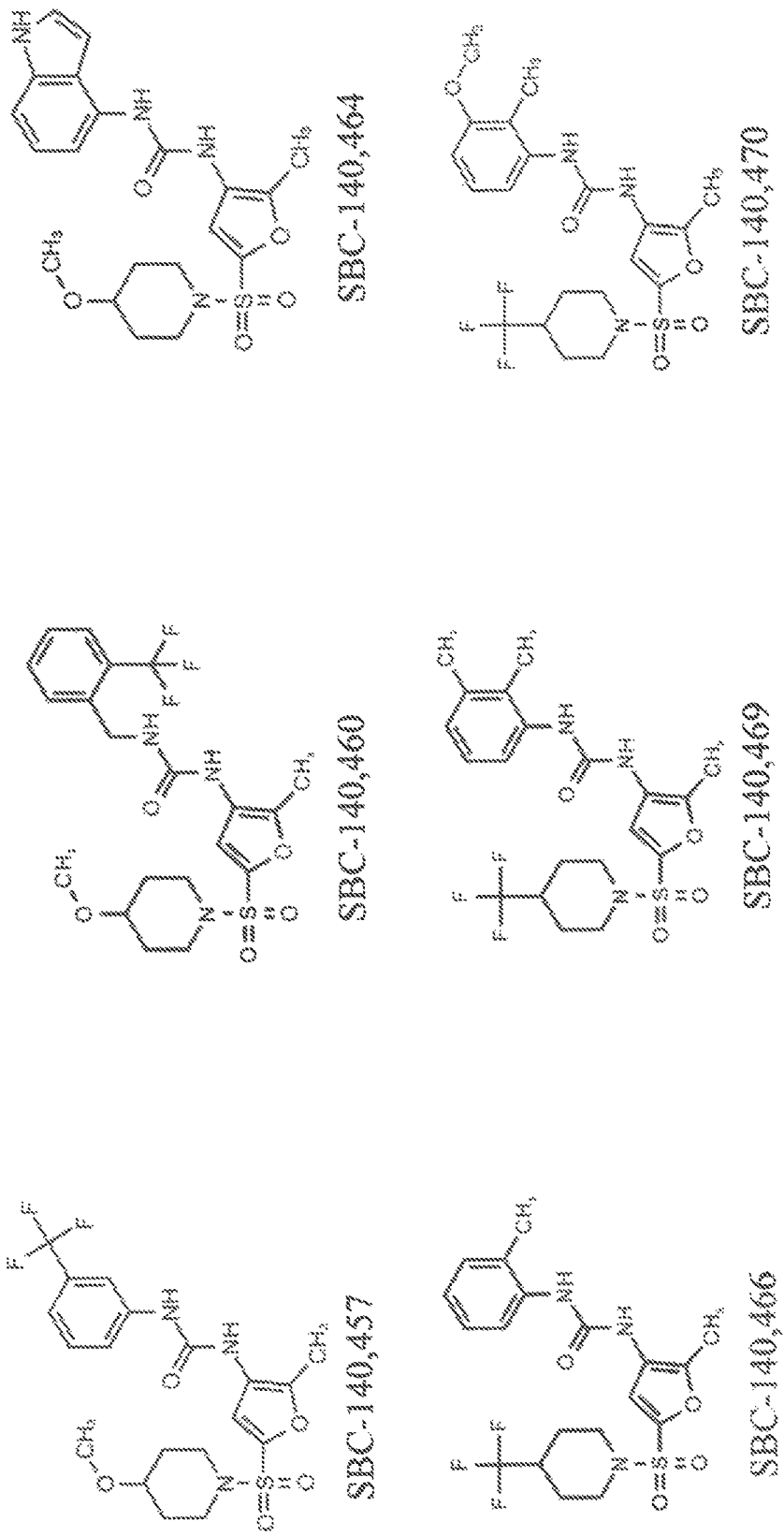

Sulfonylfuranureas were synthesized in a straightforward manner (FIG. 5). Starting with methyl 2-methyl-3-furancarboxylate (1), sulfonylation with chlorosulfonic acid was followed by treatment with $PCl_5$ to provide the sulfonyl chloride (2). Subsequent reaction with amines, $R^1R^2NH$ under standard conditions afforded sulfonamides (3). Subsequent hydrolysis provided the corresponding carboxylic acids (4), followed by a Curtius rearrangement and trapping of the intermediate isocyanate with another amine, $R^3NH_2$ to provide compounds of the general Formula (I).

The foregoing general synthetic procedures were used with commercially available starting materials to yield compounds described in FIGS. 6-9.

Example 4: Test for Compound Efficacy in Mammalian Cell Based Assay

Figure 10:
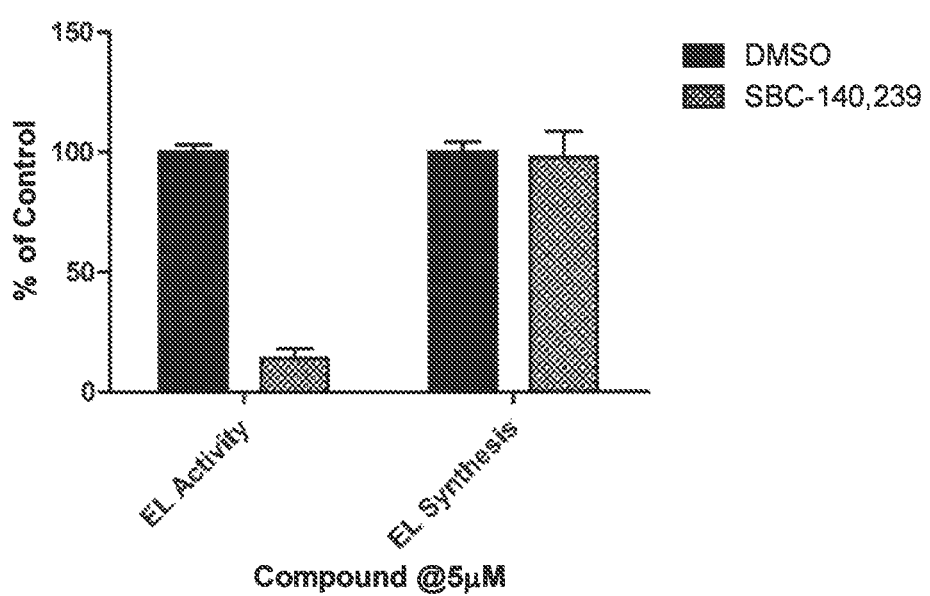
FIG. 10 graphically illustrates the efficacy of SBC-140, 239 in situ. EL cDNA construct with a C-terminal Flag tag in a mammalian expression vector was constructed and transfected in Human HEK-293 cells. Cells were incubated overnight with SBC-140,239 at 5 uM. Cells were lysed, and EL enzyme activity was determined as well as the EL expression using western blot analysis followed by quantification using the Imager GE4000.

A recombinant cell based assay was developed to determine compound efficacy, toxicity, and stability, and to confirm the mechanism of action of the compounds. A recombinant EL construct with a C-terminal Flag tag in mammalian expression vector was constructed and transfected in Human Embryonic Kidney cells. After transfection, cells were incubated overnight with compound, SBC-140,239, at 5 uM. Cells were lysed and EL enzyme activity was determined as well as expression using western blot analysis followed by quantitation using the Imager GE4000. The data shown in FIG. 10 demonstrate that an 85% inhibition of EL activity was observed at 5 uM concentration of SBC-140,239 in the cell media. No effect on EL expression was observed. This indicates that SBC-140,239 is acting primarily through inhibition of EL activity rather than the EL biosynthetic pathway.

Figure 11:
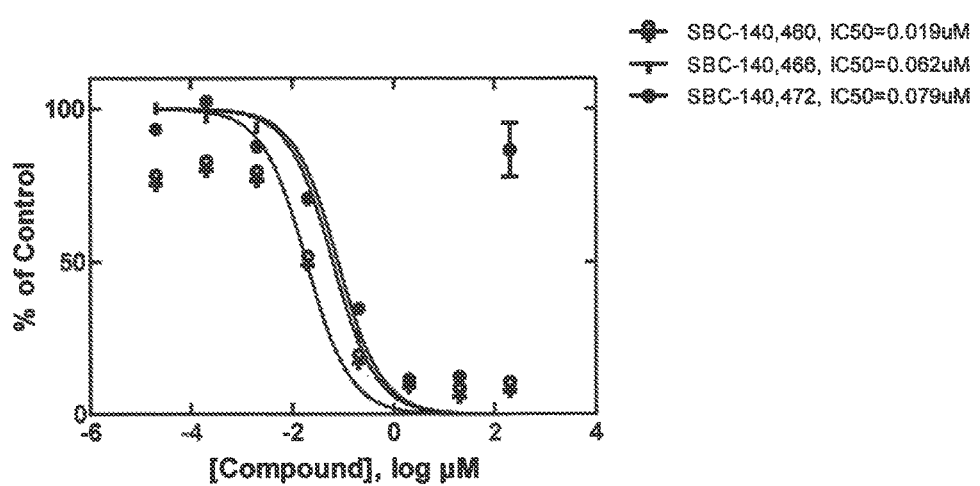
FIG. 11 graphically illustrates the potency of SBC-140, 460, SBC-140,466, and SBC-140,472. Cell extracts of HEK293/EL transfected cells were used for assaying the EL activities using various concentrations of each compound. The data presented are means of three experiments performed.

Example 5: A Structure Activity Relationship (SAR) Analysis to Improve Potency and Selectivity Additional SAR analysis around certain potent compounds of the invention was undertaken to improve potency and selectivity. Data in FIG. 11 shows the effect of certain compounds on EL activity using various concentrations of each compound ranging from 0.001-200 µM. The data shows that SBC-140,460, SBC-140,466 and SBC-140,472 exhibited an IC50 of 19, 62 nM and 79 nM, respectively. For selectivity, we tested the effect of these compounds on PL, LPL and HL activity (FIG. 12). Interestingly, although these compounds had excellent potency against EL activity, they demonstrated outstanding selectivity in that they possess no inhibition against PL, LPL and HL even at 200 uM compound concentration. Without being limited to any one theory of the invention, the presence of a 4-OMe or 4-CF3 substituent on the sulfonamide piperidine ring may be driving the superior selectivity profile observed as compared with the similarly EL potent compounds SBC-140,239, SBC-140,241, and SBC-140,244 that lack a substituent on the piperidine ring.

Example 6: Anti-Inflammatory In Vivo Testing

Figure 13:
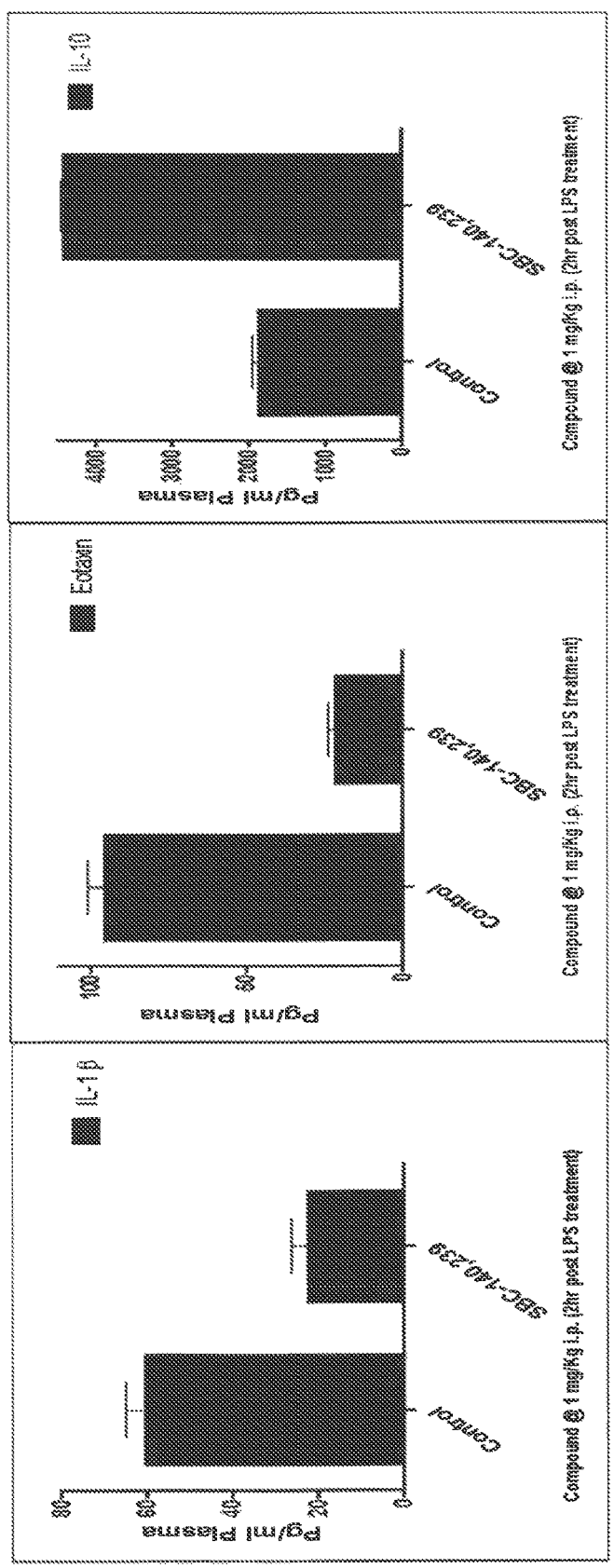
FIG. 13 graphically demonstrates certain properties of EL inhibitor, SBC-140,239, in that upon induction with lipopolysaccharides (LPS) and when compared to controls, SBC-140,239 reduces the plasma concentration of pro-inflammatory stimuli (IL-1b and eotaxin) and increases the plasma concentration of the natural anti-inflammatory mediator IL-10 in wild-type mice.

An important test for determining the utility of certain compounds of the invention is to show experimentally their biological activity in vivo. SBC-140,239 was tested for efficacy in our mouse models by measuring various functional parameters demonstrating relevant efficacy. Below is an outline of the experimental protocol used for in vivo animal studies. Briefly, male mice (C57BL/6 mice) were maintained on a 12-hour light/dark cycle and fed a chow diet. Mice were injected intraperitoneally (IP) with compounds at 1 mg/kg. Blood was obtained at different times post-administration from fasted mice under isoflurane anesthesia. Blood samples were centrifuged at 500 g for 15 minutes and plasma samples were stored at −80° C. until pharmacokinetics (PK) profiles of compounds were obtained by measuring blood levels over time using established LC/MS/MS methods. Chemokines/cytokines levels were measured using a multiplex assay. The data from FIG. 13 illustrates that SBC-140,239 exhibits good anti-inflammatory effect in that it causes the reduction of pro-inflammatory stimuli (IL-1b and eotaxin) along with a rise in the natural anti-inflammatory mediator, IL10, induced by LPS.

Example 7: Pharmacodynamics (PD) Analysis

Figure 14:
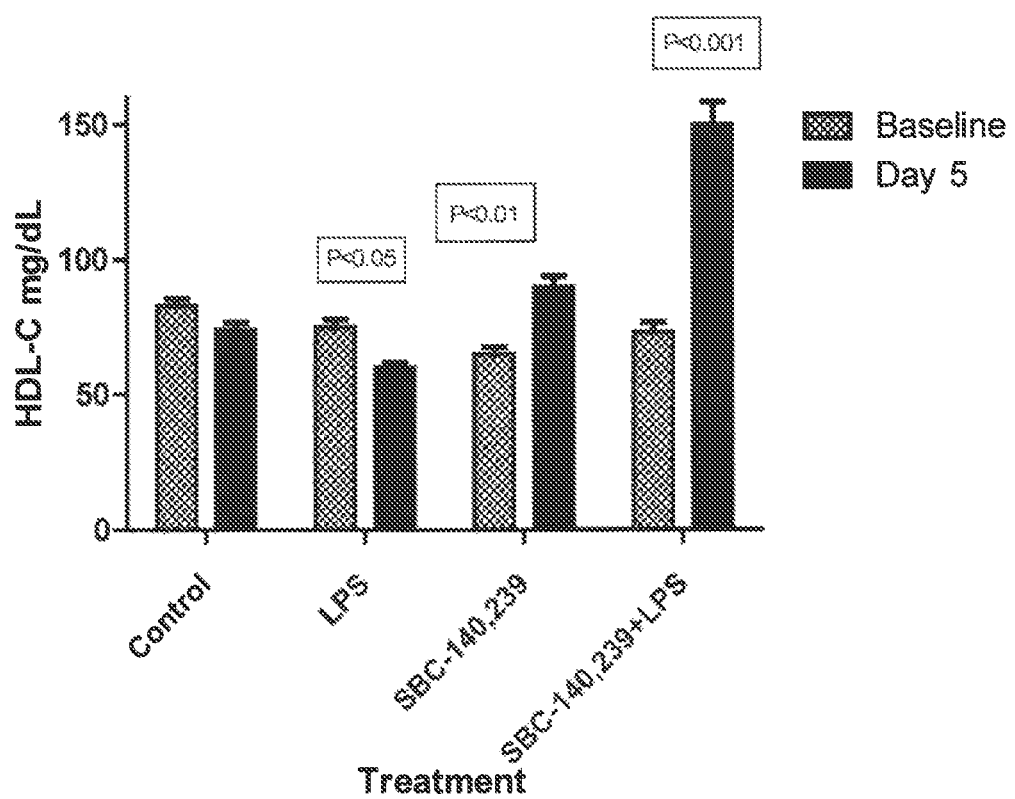
FIG. 14 graphically depicts HDL plasma levels in high fat diet fed C57/Black6 mice treated with EL inhibitor, SBC-140,239.

A nutritionally-induced hypercholesterolemia animal model was used for PD analysis. This mouse model exhibited abnormal lipid profiles and is a suitable model for examining the effects of certain compounds of the invention in increasing functional HDL levels. It is has been reported that endothelial lipase participates in HDL-C metabolism by promoting the turnover of HDL components and increasing the catabolism of apolipoprotein A-I. The aforementioned data suggest that the action of endothelial lipase on HDL may promote atherogenesis, in which case endothelial lipase may represent an attractive target for pharmaceutical intervention. The results in FIG. 14 show that in control animals the 10% decrease in HDL level after 5 days on western diet is due to an increase in the EL level mediated by inflammation. The level of HDL was further decreased by 20% in LPS treated animals. This may again be due to the increase in the EL level mediated by inflammation due to the combined LPS and high fat diet. Injection of SBC-140,239 in mice maintained on western diet resulted in an increase in the level of plasma HDL-cholesterol in non-LPS treated from 50 mg/dL to 85 mg/dL and from 65 mg/dL to 140 mg/dL in LPS treated mice. Collectively, these data suggest that inhibition of EL results in an increase in HDL associated with a decrease in the pro-inflammatory mediators and an increase in the anti-inflammatory mediators.

Example 8: Pharmacokinetics (PK) Analysis

Figure 15:
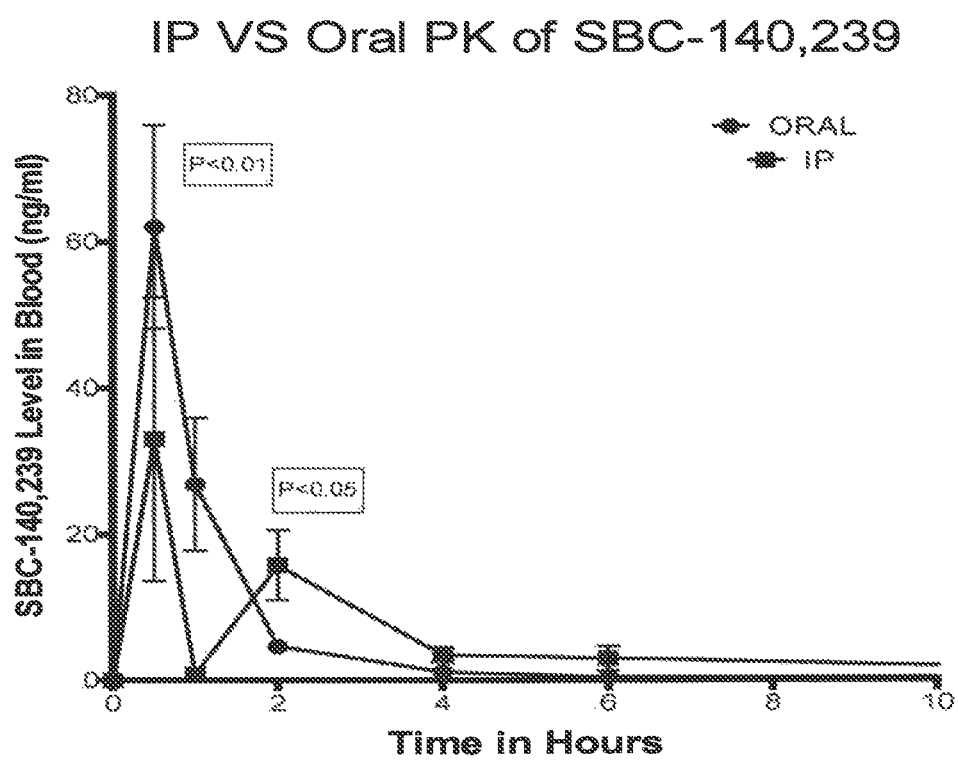
FIG. 15 graphically illustrates the intraperitoneally (IP) and oral administration of SBC-140,239 in mice and their observed amounts over time. An increased concentration of the test compound (i.e., SBC-140,239) was seen after 30 minutes of administration with 49% oral bioavailability calculated for SBC-140,239. Compound concentration in the plasma is expressed as ng/ml.

Male C57BL/6 mice, 4-5 weeks old were housed 5/cage in a room maintained at 20±2° C. with a humidity of 50±10% and a 12 h light/dark cycle. The animals were fed a standard pelleted mouse chow. Single IP and oral doses were selected (5 mg/kg) and 50 µl of blood samples were collected using anti-coagulated capillary tubes at 5 min, ½, 1, 2, 4, 6, 12, and 24 h post-administration for PK profiles using LC/MS/MS. The data in FIG. 15 shows that an increased concentration of each compound was observed after 30 minutes of administration with 49% oral bioavailability for SBC-140,239.

Example 9: Effect on Atherosclerotic Lesions

Figure 16:
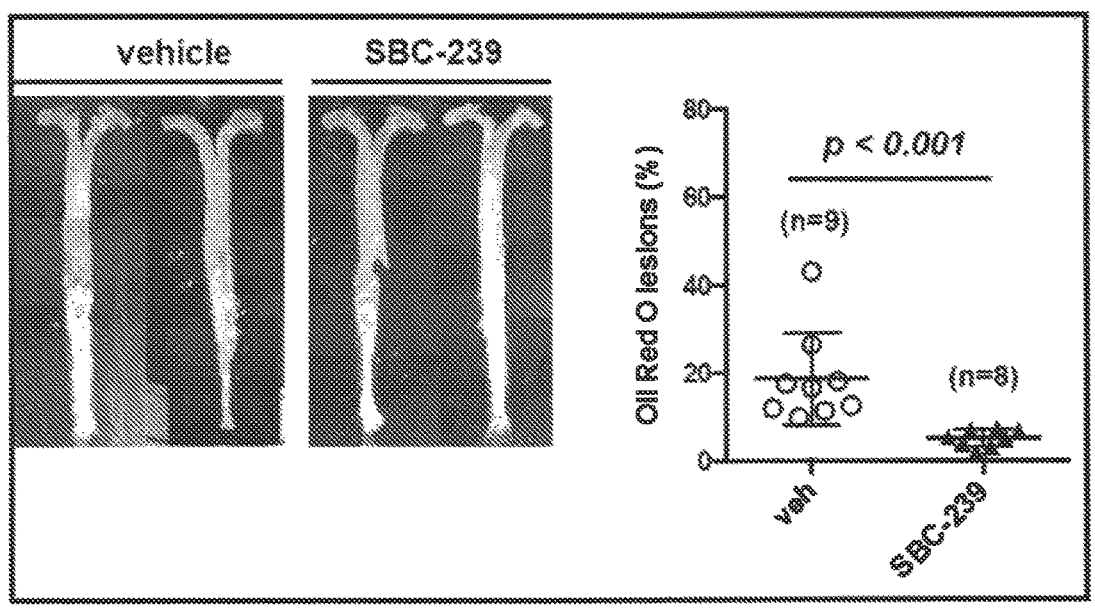
FIG. 16 graphically illustrates the beneficial effect of SBC-140,239 on the reduction of aortic lesions in ApoE-KO mice.

To evaluate the effects of the EL compound, SBC-140, 239, on the progression of atherosclerotic lesions, ApoE-KO male mice were subcutaneously implanted with osmotic mini-pumps including AngII (700 ng/kg for atherosclerosis) with/without SBC-140,239 (10 mg/kg body weight/daily) for 25 consecutive days beginning 3 days after AngII (infusion). The data in FIG. 16 shows that the lesions in control animal range between 10 to 30% occlusion. Interestingly, the effects of SBC-140,239 on the atherosclerotic lesions mice aorta were quite significant in that it resulted in reducing the lesions to less than 5% occlusion.

A number of patent and non-patent publications are cited herein in order to describe the state of the art to which this invention pertains. The entire disclosure of each of these publications is incorporated by reference herein.

While certain embodiments of the present invention have been described and/or exemplified above, various other embodiments will be apparent to those skilled in the art from the foregoing disclosure. The present invention is, therefore, not limited to the particular embodiments described and/or exemplified, but is capable of considerable variation and modification without departure from the scope and spirit of the appended claims.

Moreover, as used herein, the term "about" means that dimensions, sizes, formulations, parameters, shapes and other quantities and characteristics are not and need not be exact, but may be approximate and/or larger or smaller, as desired, reflecting tolerances, conversion factors, rounding off, measurement error and the like, and other factors known to those of skill in the art. In general, a dimension, size, formulation, parameter, shape or other quantity or characteristic is "about" or "approximate" whether or not expressly stated to be such. It is noted that embodiments of very different sizes, shapes and dimensions may employ the described arrangements.

Furthermore, the transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All compounds, compositions, and methods described herein that embody the present invention can, in alternate embodiments, be more specifically defined by any of the transitional terms "comprising," "consisting essentially of," and "consisting of."

REFERENCES

1. Spieker L E, Ruschitzka F, Luscher T F, Noll G (2004). HDL and Inflammation in Atherosclerosis. *Current Drug Targets—Immune, Endocrine & Metabolic Disorders* 4, 51-57.
2. Barter P, Nicholls S, Rye K, Anantharamaiah G, Navab-Mand Fogelman A (2004). Antiinflammatory Properties of HDL. *Circulation Research* 95, 764-772.
3. Duffy D, Rader D (2006). Emerging Therapies Targeting High-density Lipoprotein metabolism and reserve Cholesterol Transport. *Circulation* 113, 1140-1150.
4. Bruckert E, Baccara-Dinet M, McCoy F, Chapman J (2005). High prevalence of low HDL-cholesterol in a pan-European survey of 8545 dyslipidaemic patients. *Current medical research and opinion* 21, 1927-1934.
5. Aguilar-Salinas C A, Olaiz G, Valles V, Tones J M, Gomez Perez F J, Rull J A, Rojas R, Franco A, Sepulveda J (2001). High prevalence of low HDL cholesterol concentrations and mixed hyperlipidemia in a Mexican nationwide survey. *J Lipid Res* 42, 1298-1307.
6. Jaye M, Lynch K, Krawiec J, Marchadier D, Maugeais C, Doan K, South V, Amin D, Perrone M, Rader D (1999). A novel endothelial-derived lipase that modulates HDL metabolism. *Nature Genetics* 21, 424-428.
7. McCoy M G, Sun G S, Marchadier D, Maugeais C, Glick J M, Rader D J (2002). Characterization of the lipolytic activity of endothelial lipase. *J Lipid Res* 43, 921-929.
8. Ma K, Cilingiroglu M, Otvos J D, Ballantyne C M, Marian A J, Chan L (2003). Endothelial lipase is a major genetic determinant for high-density lipoprotein concentration, structure, and metabolism. *Proc Natl Acad Sci USA* 100, 2748-2753.
9. Ishida T, Choi S, Kundu R K, Hirata K, Rubin E M, Cooper A D, Quertermous T (2003). Endothelial lipase is a major determinant of HDL level. *J Clin Invest* 111, 347-355.
10. Hara T, Ishida T, Kojima Y, Tanaka H, Yasuda T, Shinohara M, Toh R, Hirata K (2011). Targeted deletion of endothelial lipase increases HDL particles with anti-inflammatory properties both in vitro and in vivo. *J Lipid Res* 52, 57-67.
11. Yasuda T, Ishida T, Rader D J (2010). Update on the role of endothelial lipase in high-density lipoprotein metabolism, reverse cholesterol transport, and atherosclerosis. *Circ J* 74, 2263-70.
12. Otera H, Ishida T, Nishiuma T, Kobayashi K, Kotani Y, Yasuda T, Kundu R K, Quertermous T, Hirata K, Nishimura Y (2009). Targeted inactivation of endothelial lipase attenuates lung allergic inflammation through raising plasma HDL level and inhibiting eosinophil infiltration. *Am J Physiol Lung Cell Mol Physiol* 296, L594-602.
13. Yasuda T, Hirata K, Ishida T, Kojima Y, Tanaka H, Okada T, Quertermous T, Yokoyama M (2007). Endothelial lipase is increased by inflammation and promotes LDL uptake in macrophages. *J Atheroscler Thromb* 14, 192-201.
14. Ishida T, Choi S, Kundu R, Spin J, Yamashita T, Hirata K, Kojima Y, Yokoyama M, Cooper A D, Quertermous T (2004). Endothelial Lipase Modulates Susceptibility to Atherosclerosis in Apolipoprotein-E-deficient Mice. *J Biol Chem* 279, 45085-45092.
15. Jin W, Millar J S, Broedl U, Glick J M, Rader D J (2003). Inhibition of endothelial lipase causes increased HDL cholesterol levels in vivo. *J Clin Invest* 111, 357-362.
16. Hutter C M, Austin M A, Farin F M, Viernes H M, Edwards K L, Leonetti D L, McNeely M J, Fujimoto W Y (2006). Association of endothelial lipase gene (LIPG) haplotypes with high-density lipoprotein cholesterol subfractions and apolipoprotein AI plasma levels in Japanese Americans. *Atherosclerosis* 185, 78-86.
17. Badellino K O, Wolfe M L, Reilly M P, and Rader D J (2006). Endothelial lipase concentrations are increased in metabolic syndrome and associated with coronary atherosclerosis. *PLoS Med* 3, e22.
18. Cox L, Birnbaum S, Mahaney M, Rainwater D, Williams J, VandeBerg J (2007). Identification of Promoter Variants in Baboon Endothelial Lipase That Regulate High-Density Lipoprotein Cholesterol Levels. *Circulation* 116, 1185-1195.
19. Choi S Y, Hirata K, Ishida T, Quertermous T, Cooper A D (2003). Endothelial lipase: a new lipase on the block. *J Lipid Res* 43, 1765-1769.
20. Keller P, Rust T, Murphy D, Matico R, Trill J, Krawiec J, Jurewicz A, Jaye M, Harpel M, Thrall S, Schwartz B (2008). A high-throughput screen for Endothelial Lipase using HDL as substrate. J. Biomolecular Screening, 13, 6, 468-475.

What is claimed is:

1. A method of treating disorders alleviated by inhibiting endothelial lipase (EL) in a patient in need of said treatment, the method comprising administering a therapeutically effective amount of at least one compound selected from the group consisting of:

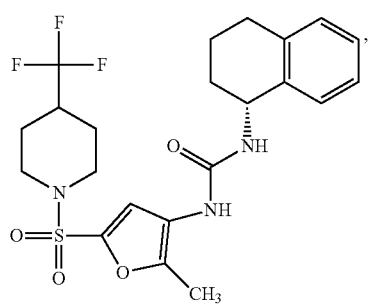
SBC-140,246

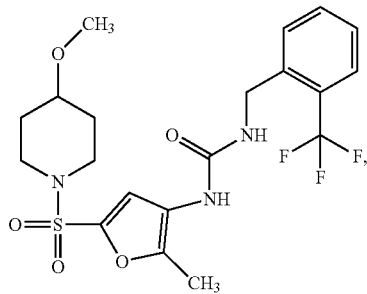
SBC-140,457

-continued

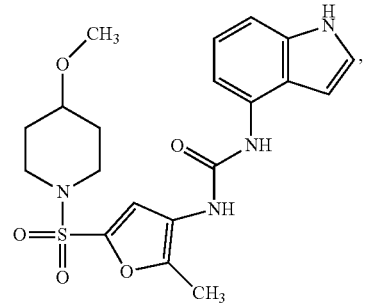
SBC-140,460

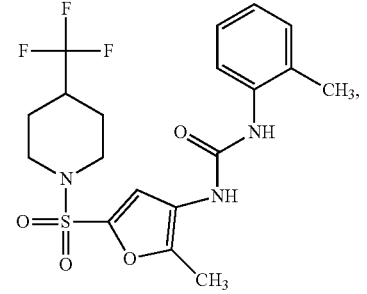
SBC-140,464

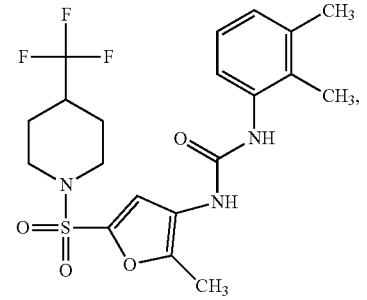
SBC-140,466

SBC-140,469

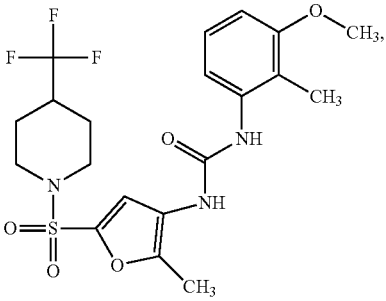
SBC-140,470

SBC-140,471

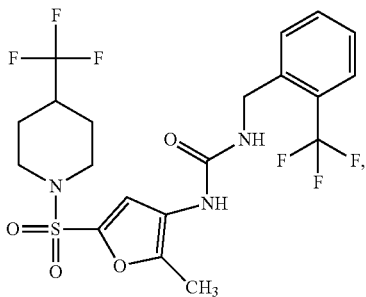

SBC-140,472

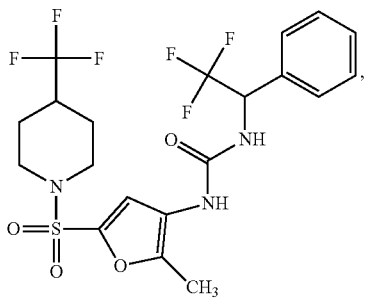

SBC-140,476

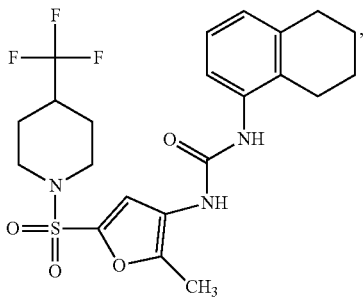

and the pharmaceutically acceptable salts, isomers, hydrates, solvates, ester or carbonate prodrugs, and complexes of said compound, wherein said disorder is selected from the group consisting of hypercholesterolemia, low HDL cholesterol, atherosclerosis, dyslipidemia, cardiovascular disease (CVD), coronary heart disease, and combinations thereof.

2. The method according to claim 1, wherein the compound is selected from the group consisting of: SBC-140,460; SBC-140,466; SBC-140,472; and the pharmaceutically acceptable salts, isomers, hydrates, solvates, ester or carbonate prodrugs, and complexes of said compound.

3. The method according to claim 1, wherein said compound is administered in dosage unit form.

4. The method according to claim 3, wherein said dosage unit includes a pharmaceutically acceptable carrier vehicle.

5. The method according to claim 1, wherein said compound is administered orally, parenterally, or by a combination thereof.

* * * * *